US007584059B2

(12) United States Patent
Bodie et al.

(10) Patent No.: US 7,584,059 B2
(45) Date of Patent: Sep. 1, 2009

(54) INHIBITION OF IMMUNE COMPLEX FORMATION

(75) Inventors: Neil M. Bodie, Agoura Hills, CA (US); Elliot Altman, Athens, GA (US)

(73) Assignee: Trinity Therapeutics, Inc., Westlake Village, CA (US)

( * ) Notice: Subject to any disclaimer, the term of this patent is extended or adjusted under 35 U.S.C. 154(b) by 469 days.

(21) Appl. No.: 11/061,065

(22) Filed: Feb. 18, 2005

(65) Prior Publication Data

US 2005/0148030 A1    Jul. 7, 2005

Related U.S. Application Data

(63) Continuation of application No. 10/131,589, filed on Apr. 24, 2002, now Pat. No. 6,916,904.

(51) Int. Cl.
*G06F 7/00* (2006.01)
(52) U.S. Cl. ............................. 702/20; 702/19; 703/11; 703/12; 703/13; 707/102
(58) Field of Classification Search ........................ None
See application file for complete search history.

(56) References Cited

U.S. PATENT DOCUMENTS

| 5,189,014 | A | | 2/1993 | Cowan, Jr. | |
|---|---|---|---|---|---|
| 5,693,758 | A | * | 12/1997 | Gould et al. | 530/350 |
| 5,821,337 | A | * | 10/1998 | Carter et al. | 530/387.3 |
| 6,319,897 | B1 | | 11/2001 | Lambris et al. | |
| 7,205,382 | B2 | | 4/2007 | Rönspeck et al. | |
| 2002/0146428 | A1 | * | 10/2002 | Hultgren et al. | 424/190.1 |
| 2004/0253247 | A1 | | 12/2004 | Dennis et al. | |

FOREIGN PATENT DOCUMENTS

| EP | 0 097 994 | 9/1987 |
|---|---|---|
| EP | 0 958 829 | 11/1999 |
| WO | WO 98/26794 | 6/1998 |
| WO | WO 00/22112 | 4/2000 |
| WO | WO 01/45746 | 6/2001 |
| WO | WO 02/38592 | 5/2002 |
| WO | WO 03/091395 | 11/2003 |

OTHER PUBLICATIONS

Abdul-Majid et al., "Fc Receptors are Critical for Autoimmune Inflammatory Damage to the Central Nervous System in Experimental Autoimmune Encephalomyelitis," *Scand. J. Immunol.*, 2002, 55:70-81.
Åsbakk et al., "An antigenic determinant is shared by psoriasis-associated p27 antigen and the Fc part of human IgG," *APMIS*, 1991, 99:551-556.
Artandi et al., "Monoclonal IgM rheumatoid factors bind IgG at a discontinuous epitope comprised of amino acid loops from heavy-chain constant-region domains 2 and 3," *Proc. Natl. Acad. Sci. USA*, 1992, 89:94-98.

Balestrieri et al. "Inhibitory Effect of IgM Rheumatoid Factor on Immune Complex Solubilization Capacity and Inhibition of Immune Precipitation," *Arthritis Rheum.*, 1984, 27(10):1130-1136.
Blom et al., "FcγR expression on macrophages is related to severity and chronicity of synovial inflammation and cartilage destruction during experimental immune-complex-mediated arthritis (ICA)," *Arthritis Res.*, 2000, 2:489-503.
Bonelli et al., "Solid phase synthesis of retro-inverso peptide analogues," *Int. J. Peptide Protein Res.*, 1984, 24:553-556.
Chen et al., "Experimental Destruction of Substantia Nigra Initiated by Parkinson Disease Immunoglobulins," *Arch. Neurol.*, 1998, 55:1075-1080.
Clot et al., "Immunological aspects of psoriasis," *Br. J. Dermatol.*, 1978, 99:25-30.
Clynes et al., "Fc receptors are required in passive and active immunity to melanoma," *Proc. Natl. Acad. Sci. USA*, 1998, 95:652-656.
Clynes et al., "Uncoupling of Immune Complex Formation and Kidney Damage in Autoimmune Glomerulonephritis," *Science*, 1998, 279:1052-1054.
Clynes et al., "Inhibitory Fc receptors modulate in vivo cytoxicity against tumor targets," *Nature Medicine*, 2000, 6(4):443-446.
Corper et al., "Structure of human IgM rheumatoid factor Fab bound to its autoantigen IgG Fc reveals a novel topology of antibody-antigen interaction," *Nat. Struct. Biol.*, 1997, 4(5):374-381.
Coxon et al., "FcγRIII Mediates Neutrophil Recruitment to Immune Complexes: A Mechanism for Neutrophil Accumulation in Immune-Mediated Inflammation," *Immunity*, 2001, 14:693-704.
Coyle and Procyk-Dougherty, "Multiple Sclerosis Immune Complexes: An Analysis of Component Antigens and Antibodies," *Ann. Neurol.*, 1984, 16:660-667.
Dalaker et al., "Expression of the Psoriasis-associated Antigen, Pso p27, in Inhibited by Cyclosporin A," *Acta Derm. Venereol.*, 1999, 79:281-284.
DeLano et al., "Convergent Solutions to Binding at a Protein-Protein Interface," *Science*, 2000, 287:1279-1283.
Easterbrook-Smith et al., "The Role of Fc:Fc Interactions in Insoluble Immune Complex Formation and Complement Activation," *Mol. Immunol.*, 1988, 25(12):1331-1337.
Elmgreen et al., "Demonstration of Circulating Immune Complexes by the Indirect Leucocyte Phagocytosis Test in Chronic Inflammatory Bowel Disease," *Acta Med. Scand.*, 1985, 218:73-78.
Ezaki et al., "Human monoclonal rheumatoid factors augment arthritis in mice by the activation of T cells," *Clin. Exp. Immunol.*, 1996, 104:474-482.

(Continued)

*Primary Examiner*—Mary K Zeman
(74) *Attorney, Agent, or Firm*—Fish & Richardson P.C.

(57) ABSTRACT

Polypeptides and other compounds that can bind specifically to the $C_H2$-$C_H3$ cleft of an immunoglobulin molecule, and methods for using such polypeptides and compounds to inhibit Fc-mediated immune complex formation, are described.

24 Claims, 11 Drawing Sheets

OTHER PUBLICATIONS

Figure 1A:
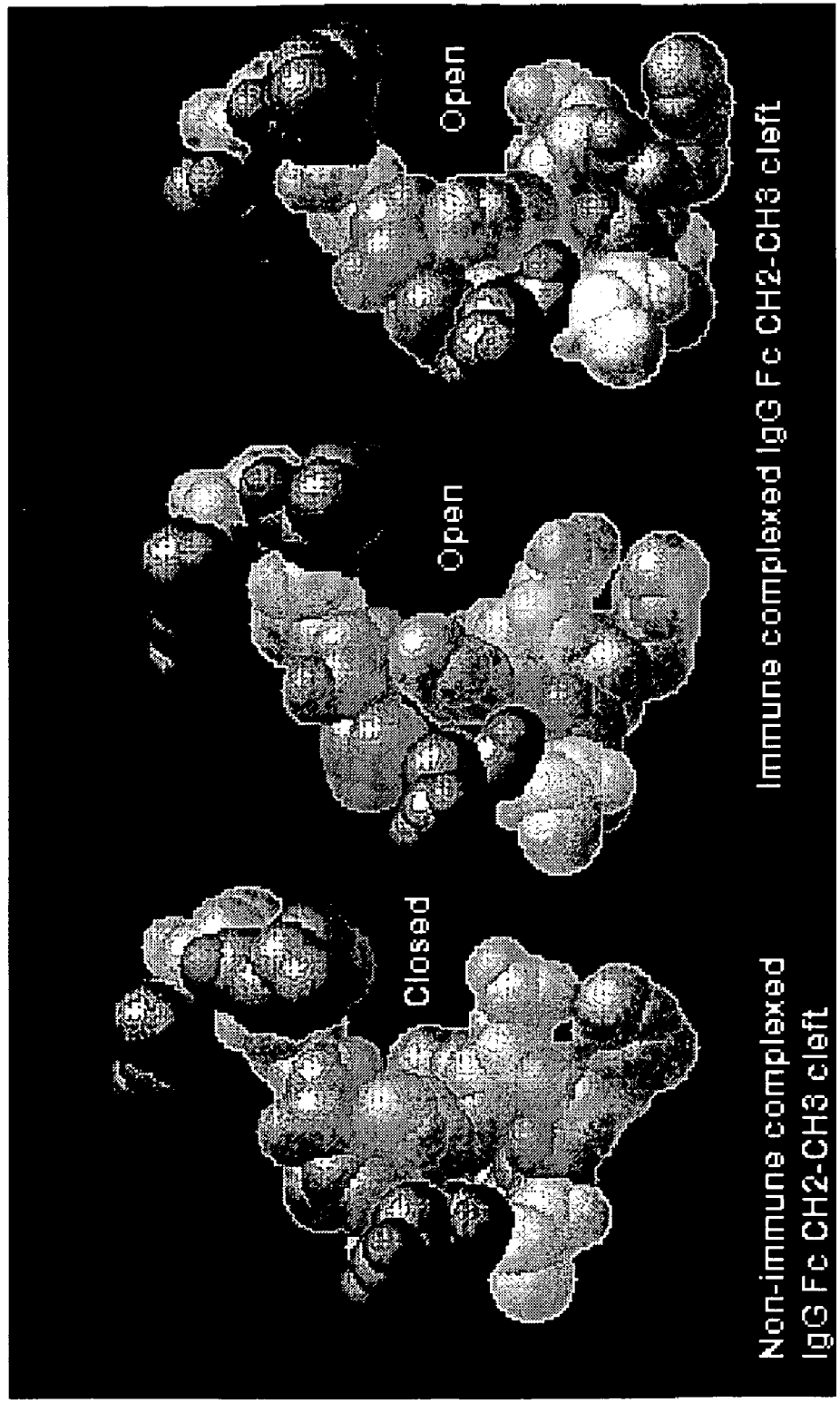

Fossati et al., "Fcγ receptors in autoimmune diseases," *Eur. J. Clin. Invest.*, 2001, 31:821-831.

Frangione and Milstein, "Variations in the S-S Bridges of Immunoglobins G: Interchain Disulphide Bridges of γG3 Myeloma Proteins," *J. Mol. Biol.*, 1968: 33:893-906.

Gergely and Sármay, "Fcγ Receptors in Malignancies: Friends or Enemies?" *Adv. Cancer Res.*, 1994, 64:211-245.

Ghetie and Ward, "Multiple Roles for the Major Histocompatibility Complex Class I-Related Receptor $F_cR_N$," *Annu. Rev. Immunol.*, 2000, 18:739-766.

Girkontaite et al., "Immunochemical Study of Human Immunoglobulin G Fc Region," *Cancer Biother. Radiopharm.*, 1996, 11:87-96.

Glader et al., "The proatherogenic properties of lipoprotein(a) may be enhanced through the formation of circulating immune complexes containing *Chlamydia pneumoniae*-specific IgG antibodies," *Eur. Heart J.*, 2000, 21:639-646.

Gómez-Guerrero et al., "Administeration of IgG Fc Fragments Prevents Glomerular Injury in Experimental Immune Complex Nephritis," *J. Immunol.*, 2000, 164:2092-2101.

Guddat et al., "Local and Transmitted Conformational Changes on Complexation of an Anti-sweetener Fab," *J. Mol. Biol.*, 1994, 236:247-274.

Gussin et al., "Effect of circulating immune complexes on the binding of rheumatoid factor to histones," *Ann. Rheum. Dis.*, 2000, 59:351-358.

Gussin et al., "Noncognate Binding to Histones of IgG from Patients with Idiopathic Systemic Lupus Erythematosus," *Clin. Immunol.*, 2000, 96(2):150-161.

Hamano et al., "Immune Complex and Fc Receptor-Mediated Augmentation of Antigen Presentation for in Vivo Th Cell Responses," *J. Immunol.*, 2000, 164:6113-6119.

Harris et al., "Refined Structure of an Intact IgG2a Monoclonal Antibody," *Biochemistry*, 1997, 36:1581-1597.

Holmdahl et al., "Generation of Monoclonal Rheumatoid Factors after Immunization with Collagen II-Anti-Collagen II Immune Complexes," *Scand. J. Immunol.*, 1986, 24:197-203.

Hoover et al., "Modulation of Growth and Differentiation of Murine Myeloma Cells by Immunoglobulin Binding Factors," *Curr. Top. Microbiol. Immunol.*, 1990, 166:77-85.

Iivanainen, "The significance of abnormal immune responses in patients with multiple sclerosis," *J. Neuroimmunol.*, 1981, 1:141-172.

Jackson, "Contributions of Protein Structure-Based Drug Design to Cancer Chemotherapy," *Sem. Oncol.*, 1997, 24(2):164-172.

Jefferis et al., "Immunogenic and Antigenic Epitopes of Immunoglobulins. VIII. A Human Monoclonal Rheumatoid Factor Having Specificity for a Discontinuous Epitope Determined by Histidine/Arginine Interchange as Residue 435 of Immunoglobulin G," *Immunol. Lett.*, 1984, 7:191-194.

Jones et al., "Structure-Based Design of Lipophilic Quinazoline Inhibitors of Thymidylate Synthase," *J. Med. Chem.*, 1996, 39:904-917.

Kabat et al., *Sequences of Proteins of Immunological Interest*, Fourth Edition, 1987, U.S. Department of Health and Human Services, Public Health Service National Institutes of Health, 1987, (Table of Contents only).

Kleinau et al., "Induction and Suppression of Collagen-induced Arthritis Is Dependent on Distinct Fcγ Receptors," *J. Exp. Med.*, 2000, 191(9):1611-1616.

Koroleva et al., "Binding of complement subcomponent C1q to *Streptococcus pyogenes*: evidence for interactions with the M5 and FcRA76 proteins," *FEMS Immunol. Med. Microbiol.*, 1998, 20:11-20.

Leach et al., "Isolation from Human Placenta of the IgG Transporter, FcRn, and Localization to the Syncytiotrophoblast," *J. Immunol.*, 1996, 157:3317-3322.

Liu et al., "$\beta_2$-microglobulin-deficient Mice Are Resistant to Bullous Pemphigoid," *J. Exp. Med.*, 1997, 186(5):777-783.

Manzi et al., "Inflammation-mediated rheumatic diseases and atherosclerosis," *Ann. Rheum. Dis.*, 2000, 59(5):321-325.

Marino et al., "Prevention of systemic lupus erythematosus in MRL/lpr mice by administration of an immunoglobulin-binding peptide," *Nature Biotechnol.*, 2000, 18:735-739.

Mathiot et al., "In vitro Inhibition of Tumor B Cell Growth by IgG-BF Producing FcγRII+ T Cell Hybridoma and by Immunoglobulin G-Binding Factors," *Immunol. Res.*, 1992, 11:296-304.

Møller, "Fc-mediated immune precipitation," *Immunology*, 1979, 38:631-640.

Møller and Steensgaard, "Fc-mediated immune precipitation," *Immunology*, 1979, 38:641-648.

Møller and Christiansen, "Fc-mediated immune precipitation," *Immunology*, 1983, 48:469.

Møller and Pedersen, "Fc-mediated immune precipitation," *Immunology*, 1983, 48:477-488.

Nardella et al., "IgG Rheumatoid Factors and Staphylococcal Protein A Bind to a Common Molecular Site on IgG," *J. Exp. Med.*, 1985, 162:1811-1824.

Nardella et al., "T15 Group A Streptococcal Fc Receptor Binds to the Same Location on IgG As Staphylococcal Protein A and IgG Rheumatoid Factors," *J. Immunol.*, 1987, 138:922-926.

Nielsen et al. "Release of leukotriene B4 and 5-hydroxyeicosatetraenoic acid during phagocytosis of artificial immune complexes by peripheral neutrophils in chronic inflammatory bowel disease," *Clin. Exp. Immunol.*, 1986, 65:465-471.

O'Brien et al., "The Effects of Histidine Residue Modification on the Immune Precipitating Ability of Rabbit IgG," *Arch. Biochem. Biophys.*, 1994, 310:25-31.

Padlan, "Anatomy of the Antibody Molecule," *Mol. Immunol.*, 1994, 31(3):169-217.

Pasceri and Yeh, "A Tale of Two Diseases—Atherosclerosis and Rheumatoid Arthritis," *Circulation*, 1999, 100:2124-2126.

Poston, "Basic Proteins Bind Immunoglobulin G: A Mechanism for Demyelinating Disease?" *Lancet*, 1984, 1:1268-1271.

Procaccia et al., "Circulating immune complexes in serum and in cerebrospinal fluid of patients with multiple sclerosis," *Acta Neurol. Scand.*, 1988, 77:373-381.

Procaccia et al. "Detection of rheumatoid factors of different isotypes and of circulating immune complexes in patients with inflammatory bowel disease," *Boll Ist Sieroter Milan*, 1990, 69(2):413-421 (Abstract only).

Raghavan and Bjorkman, "Fc Receptors and Their Interactions with Immunoglobulins," *Annu. Rev. Cell Dev. Biol.*, 1996, 12:181-220.

Ratcliffe et al., "Immunocytochemical detection of Fcγ receptors in human atherosclerotic lesions," *Immunol. Lett.*, 2001, 77:169-174.

Rødahl et al., "Participation of antigens related to the psoriasis associated antigen, pso p27, in immune complex formation in patients with ankylosing spondylitis," *Ann. Rheum. Dis.*, 1988, 47:628-633.

Sahu et al. "Binding Kinetics, Structure-Activity Relationship, and Biotransformation of the Complement Inhibitor Compstatin," *J. Immunol.*, 2000, 165:2491-2499.

Saphire et al., "A New Look at Rheumatoid Factor," *Cutting Edge Reports*, from http://www.rheuma21st.com—pp. 1-9.

Saphire et al., "Crystal Structure of a Neutralizing Human IgG Against HIV-1: A Template for Vaccine Design," *Science*, 2001, 293:1155-1159.

Sasso et al., "Antigenic Specificities of Human Monoclonal and Polyclonal IgM Rheumatoid Factors," *J. Immunol.*, 1988, 140(9):3098-3107.

Shields et al., "High Resolution Mapping of the Binding Site on Human IgG1, for γRI, γRII, γRIII, and FcRn and Design of IgG1 Variants with Improved Binding to the γR," *J. Biol. Chem.*, 2001, 276(9):6591-6604.

Sindic et al., "The binding of myelin basic protein to the Fc region of aggregated IgG and to immune complexes," *Clin. Exp. Immunol.*, 1980:41:1-7.

Sohi et al., "Crystallization of a complex between the Fab fragment of a human immunoglobulin M (IgM) rheumatoid factor (RF-AN) and the Fc fragment of human IgG4," *Immunology*, 1996, 88:636-641.

Stone et al., "The Fc Binding Site for Streptococcal Protein G is in the Cγ2-Cγ3 Interface Region of IgG and is Related to the Sites That Bind Staphylococcal Protein A and Human Rheumatoid Factors," *J. Immunol.*, 1989, 143(2):565-570.

Sulica et al. "Effect of protein A of *Staphylococcus aureus* on the binding of monomeric and polymeric IgG to Fc receptor-bearing cells," *Immunology*, 1979, 38:173-179.

Termaat et al., "Anti-DNA antibodies can bind to the glomerulus via two distinct mechanisms," *Kidney Int.*, 1992, 42:1363-1371.

Vedeler et al., "Fc receptors for immunoglobulin G—a role in the pathogenesis of Guillain-Barré syndrome and multiple sclerosis," *J. Neuroimmunol.*, 2001, 118:187-193.

Verdini and Viscomi, "Synthesis, Resolution, and Assignment of Configuration of Potent Hypotensive Retro-inverso Bradykinin Potentiating Peptide 5a($BPP_{5a}$) Analogues," *J. Chem. Soc. Perkin Trans. I*, 1985, 1:697-701.

Wallace et al., "Role of Fcγ receptors in cancer and infectious disease," *J. Leukocyte Biol.*, 1994, 55:816-826.

West, Jr. and Bjorkman, "Crystal Structure and Immunoglobulin G Binding Properties of the Human Major Histocompatibility Complex-Related Fc Receptor," *Biochemistry*, 2000, 39:9698-9708.

Wines et al., "The IgG Fc Contains Distinct Fc Receptor (FcR) Binding Sites: The Leukocyte Receptors FcγRI and FcγRIIa Bind to a Region in the Fc Distinct from That Recognized by Neonatal FcR and Protein A," *J. Immunol.*, 2000, 164:5313-5318.

Witz and Ran, "FcR May Function as a Progression Factor of Nonlymphoid Tumors," *Immunol. Res.*, 1992, 11:283-295.

Zack et al., "Localization of an Fc-Binding Reactivity to the Constant Region of Human IgG4," *J. Immunol.*, 1995, 155:5057-5063.

Boren and Gershwin, "Inflamm-aging: autoimmunity, and the immune-risk phenotype," *Autoimmunity Rev.*, 3:401-406, 2004.

Solomon, "Intravenous immunoglobulin and Alzheimer's disease immunotherapy," *Curr. Opin. Mol. Therapeutics*, 9(1):79-85, 2007.

Theodore et al., "Targeted overexpression of human α-synuclein triggers microglial activation and adaptive immune response in a mouse model of Parkinson disease," *J. Neuropath. Exp. Neurol.*, 67(12):1149-1158, 2008.

* cited by examiner

Figure 2A

| ATOM | 1865 | N | LEU | A 251 | 27.507 | 31.617 | 11.391 | 1.00 | 19.12 | N |
|------|------|------|------|-------|--------|--------|--------|------|-------|---|
| ATOM | 1866 | CA | LEU | A 251 | 27.327 | 31.886 | 12.816 | 1.00 | 18.21 | C |
| ATOM | 1867 | C | LEU | A 251 | 28.563 | 32.344 | 13.599 | 1.00 | 19.13 | C |
| ATOM | 1868 | O | LEU | A 251 | 28.433 | 32.877 | 14.706 | 1.00 | 18.20 | O |
| ATOM | 1869 | CB | LEU | A 251 | 26.730 | 30.649 | 13.489 | 1.00 | 18.15 | C |
| ATOM | 1870 | CG | LEU | A 251 | 25.417 | 30.137 | 12.891 | 1.00 | 15.85 | C |
| ATOM | 1871 | CD1 | LEU | A 251 | 25.009 | 28.822 | 13.509 | 1.00 | 12.87 | C |
| ATOM | 1872 | CD2 | LEU | A 251 | 24.350 | 31.174 | 13.098 | 1.00 | 14.96 | C |
| ATOM | 1873 | N | MET | A 252 | 29.754 | 32.076 | 13.067 | 1.00 | 19.47 | N |
| ATOM | 1874 | CA | MET | A 252 | 30.998 | 32.483 | 13.718 | 1.00 | 17.57 | C |
| ATOM | 1875 | C | MET | A 252 | 31.631 | 33.635 | 12.942 | 1.00 | 19.19 | C |
| ATOM | 1876 | O | MET | A 252 | 31.917 | 33.509 | 11.751 | 1.00 | 19.47 | O |
| ATOM | 1877 | CB | MET | A 252 | 31.986 | 31.324 | 13.778 | 1.00 | 17.49 | C |
| ATOM | 1878 | CG | MET | A 252 | 31.569 | 30.181 | 14.680 | 1.00 | 20.45 | C |
| ATOM | 1879 | SD | MET | A 252 | 32.867 | 28.921 | 14.831 | 1.00 | 22.74 | S |
| ATOM | 1880 | CE | MET | A 252 | 33.894 | 29.668 | 16.021 | 1.00 | 17.91 | C |
| ATOM | 1881 | N | ILE | A 253 | 31.863 | 34.751 | 13.628 | 1.00 | 20.54 | N |
| ATOM | 1882 | CA | ILE | A 253 | 32.458 | 35.946 | 13.026 | 1.00 | 18.92 | C |
| ATOM | 1883 | C | ILE | A 253 | 33.930 | 35.709 | 12.677 | 1.00 | 20.20 | C |
| ATOM | 1884 | O | ILE | A 253 | 34.529 | 36.465 | 11.901 | 1.00 | 20.88 | O |
| ATOM | 1885 | CB | ILE | A 253 | 32.320 | 37.157 | 13.973 | 1.00 | 15.28 | C |
| ATOM | 1886 | CG1 | ILE | A 253 | 32.613 | 38.463 | 13.235 | 1.00 | 17.06 | C |
| ATOM | 1887 | CG2 | ILE | A 253 | 33.246 | 36.996 | 15.160 | 1.00 | 16.38 | C |
| ATOM | 1888 | CD1 | ILE | A 253 | 31.683 | 38.772 | 12.079 | 1.00 | 11.72 | C |
| ATOM | 1889 | N | SER | A 254 | 34.506 | 34.648 | 13.232 | 1.00 | 19.05 | N |
| ATOM | 1890 | CA | SER | A 254 | 35.891 | 34.327 | 12.945 | 1.00 | 21.13 | C |
| ATOM | 1891 | C | SER | A 254 | 36.056 | 33.485 | 11.673 | 1.00 | 22.40 | C |
| ATOM | 1892 | O | SER | A 254 | 37.172 | 33.069 | 11.354 | 1.00 | 22.89 | O |
| ATOM | 1893 | CB | SER | A 254 | 36.538 | 33.628 | 14.143 | 1.00 | 19.91 | C |
| ATOM | 1894 | OG | SER | A 254 | 35.833 | 32.459 | 14.508 | 1.00 | 19.27 | O |
| ATOM | 1895 | N | ARG | A 255 | 34.954 | 33.225 | 10.961 | 1.00 | 23.38 | N |
| ATOM | 1896 | CA | ARG | A 255 | 34.993 | 32.434 | 9.726 | 1.00 | 23.13 | C |
| ATOM | 1897 | C | ARG | A 255 | 34.419 | 33.198 | 8.553 | 1.00 | 24.34 | C |
| ATOM | 1898 | O | ARG | A 255 | 33.769 | 34.220 | 8.740 | 1.00 | 24.57 | O |
| ATOM | 1899 | CB | ARG | A 255 | 34.269 | 31.100 | 9.883 | 1.00 | 21.88 | C |
| ATOM | 1900 | CG | ARG | A 255 | 34.885 | 30.244 | 10.941 | 1.00 | 23.18 | C |
| ATOM | 1901 | CD | ARG | A 255 | 34.572 | 28.781 | 10.796 | 1.00 | 25.79 | C |
| ATOM | 1902 | NE | ARG | A 255 | 35.225 | 28.072 | 11.892 | 1.00 | 35.87 | N |
| ATOM | 1903 | CZ | ARG | A 255 | 35.179 | 26.760 | 12.098 | 1.00 | 37.69 | C |
| ATOM | 1904 | NH1 | ARG | A 255 | 34.501 | 25.970 | 11.273 | 1.00 | 39.85 | N |
| ATOM | 1905 | NH2 | ARG | A 255 | 35.811 | 26.243 | 13.147 | 1.00 | 35.85 | N |
| ATOM | 3301 | N | GLU | X 430 | 21.640 | 30.893 | 14.939 | 1.00 | 15.96 | N |
| ATOM | 3302 | CA | GLU | X 430 | 21.482 | 32.343 | 14.837 | 1.00 | 16.83 | C |
| ATOM | 3303 | C | GLU | X 430 | 20.580 | 33.002 | 15.882 | 1.00 | 17.49 | C |
| ATOM | 3304 | O | GLU | X 430 | 20.808 | 34.155 | 16.254 | 1.00 | 16.39 | O |
| ATOM | 3305 | CB | GLU | X 430 | 21.001 | 32.737 | 13.435 | 1.00 | 18.58 | C |
| ATOM | 3306 | CG | GLU | X 430 | 19.587 | 32.290 | 13.103 | 1.00 | 24.20 | C |
| ATOM | 3307 | CD | GLU | X 430 | 19.055 | 32.908 | 11.825 | 1.00 | 26.67 | C |
| ATOM | 3308 | OE1 | GLU | X 430 | 18.935 | 32.176 | 10.812 | 1.00 | 29.85 | O |
| ATOM | 3309 | OE2 | GLU | X 430 | 18.760 | 34.124 | 11.834 | 1.00 | 26.94 | O |
| ATOM | 3310 | N | ALA | X 431 | 19.564 | 32.273 | 16.343 | 1.00 | 16.87 | N |
| ATOM | 3311 | CA | ALA | X 431 | 18.598 | 32.793 | 17.306 | 1.00 | 17.47 | C |
| ATOM | 3312 | C | ALA | X 431 | 19.015 | 32.786 | 18.770 | 1.00 | 18.82 | C |

Figure 2A

| ATOM | 3313 | O   | ALA | X 431 | 18.273 | 33.282 | 19.631 | 1.00 | 19.27 | O |
|------|------|-----|-----|-------|--------|--------|--------|------|-------|---|
| ATOM | 3314 | CB  | ALA | X 431 | 17.288 | 32.077 | 17.149 | 1.00 | 18.26 | C |
| ATOM | 3315 | N   | LEU | X 432 | 20.158 | 32.165 | 19.054 | 1.00 | 19.02 | N |
| ATOM | 3316 | CA  | LEU | X 432 | 20.696 | 32.092 | 20.412 | 1.00 | 17.81 | C |
| ATOM | 3317 | C   | LEU | X 432 | 21.410 | 33.407 | 20.693 | 1.00 | 20.18 | C |
| ATOM | 3318 | O   | LEU | X 432 | 21.801 | 34.118 | 19.754 | 1.00 | 21.08 | O |
| ATOM | 3319 | CB  | LEU | X 432 | 21.702 | 30.938 | 20.524 | 1.00 | 13.24 | C |
| ATOM | 3320 | CG  | LEU | X 432 | 21.173 | 29.498 | 20.601 | 1.00 | 11.17 | C |
| ATOM | 3321 | CD1 | LEU | X 432 | 22.246 | 28.492 | 20.229 | 1.00 | 5.93  | C |
| ATOM | 3322 | CD2 | LEU | X 432 | 20.665 | 29.229 | 21.999 | 1.00 | 8.08  | C |
| ATOM | 3323 | N   | HIS | X 433 | 21.559 | 33.764 | 21.968 | 1.00 | 19.77 | N |
| ATOM | 3324 | CA  | HIS | X 433 | 22.280 | 34.996 | 22.278 | 1.00 | 18.30 | C |
| ATOM | 3325 | C   | HIS | X 433 | 23.717 | 34.699 | 21.888 | 1.00 | 17.74 | C |
| ATOM | 3326 | O   | HIS | X 433 | 24.301 | 33.731 | 22.381 | 1.00 | 17.19 | O |
| ATOM | 3327 | CB  | HIS | X 433 | 22.221 | 35.329 | 23.763 | 1.00 | 19.01 | C |
| ATOM | 3328 | CG  | HIS | X 433 | 23.120 | 36.462 | 24.161 | 1.00 | 15.62 | C |
| ATOM | 3329 | ND1 | HIS | X 433 | 22.844 | 37.778 | 23.855 | 1.00 | 16.17 | N |
| ATOM | 3330 | CD2 | HIS | X 433 | 24.283 | 36.474 | 24.856 | 1.00 | 13.22 | C |
| ATOM | 3331 | CE1 | HIS | X 433 | 23.797 | 38.551 | 24.346 | 1.00 | 14.33 | C |
| ATOM | 3332 | NE2 | HIS | X 433 | 24.682 | 37.785 | 24.956 | 1.00 | 12.05 | N |
| ATOM | 3333 | N   | ASN | X 434 | 24.255 | 35.489 | 20.967 | 1.00 | 16.58 | N |
| ATOM | 3334 | CA  | ASN | X 434 | 25.621 | 35.300 | 20.489 | 1.00 | 16.67 | C |
| ATOM | 3335 | C   | ASN | X 434 | 25.765 | 34.004 | 19.682 | 1.00 | 15.91 | C |
| ATOM | 3336 | O   | ASN | X 434 | 26.881 | 33.500 | 19.487 | 1.00 | 12.49 | O |
| ATOM | 3337 | CB  | ASN | X 434 | 26.623 | 35.307 | 21.649 | 1.00 | 15.89 | C |
| ATOM | 3338 | CG  | ASN | X 434 | 26.930 | 36.702 | 22.150 | 1.00 | 20.56 | C |
| ATOM | 3339 | OD1 | ASN | X 434 | 26.848 | 37.685 | 21.401 | 1.00 | 19.24 | O |
| ATOM | 3340 | ND2 | ASN | X 434 | 27.301 | 36.802 | 23.430 | 1.00 | 22.26 | N |
| ATOM | 3341 | N   | HIS | X 435 | 24.637 | 33.489 | 19.192 | 1.00 | 14.58 | N |
| ATOM | 3342 | CA  | HIS | X 435 | 24.630 | 32.263 | 18.401 | 1.00 | 15.75 | C |
| ATOM | 3343 | C   | HIS | X 435 | 25.235 | 31.111 | 19.194 | 1.00 | 16.92 | C |
| ATOM | 3344 | O   | HIS | X 435 | 25.654 | 30.115 | 18.604 | 1.00 | 18.53 | O |
| ATOM | 3345 | CB  | HIS | X 435 | 25.467 | 32.424 | 17.115 | 1.00 | 15.28 | C |
| ATOM | 3346 | CG  | HIS | X 435 | 25.045 | 33.565 | 16.230 | 1.00 | 14.75 | C |
| ATOM | 3347 | ND1 | HIS | X 435 | 25.857 | 34.056 | 15.226 | 1.00 | 12.80 | N |
| ATOM | 3348 | CD2 | HIS | X 435 | 23.909 | 34.293 | 16.185 | 1.00 | 12.14 | C |
| ATOM | 3349 | CE1 | HIS | X 435 | 25.233 | 35.037 | 14.601 | 1.00 | 11.07 | C |
| ATOM | 3350 | NE2 | HIS | X 435 | 24.051 | 35.204 | 15.159 | 1.00 | 12.23 | N |
| ATOM | 3351 | N   | TYR | X 436 | 25.249 | 31.210 | 20.520 | 1.00 | 17.92 | N |
| ATOM | 3352 | CA  | TYR | X 436 | 25.863 | 30.161 | 21.331 | 1.00 | 19.32 | C |
| ATOM | 3353 | C   | TYR | X 436 | 25.198 | 29.910 | 22.694 | 1.00 | 21.37 | C |
| ATOM | 3354 | O   | TYR | X 436 | 24.517 | 30.772 | 23.263 | 1.00 | 24.74 | O |
| ATOM | 3355 | CB  | TYR | X 436 | 27.354 | 30.493 | 21.528 | 1.00 | 15.83 | C |
| ATOM | 3356 | CG  | TYR | X 436 | 28.235 | 29.346 | 21.976 | 1.00 | 13.27 | C |
| ATOM | 3357 | CD1 | TYR | X 436 | 28.732 | 29.283 | 23.281 | 1.00 | 15.99 | C |
| ATOM | 3358 | CD2 | TYR | X 436 | 28.618 | 28.352 | 21.082 | 1.00 | 14.84 | C |
| ATOM | 3359 | CE1 | TYR | X 436 | 29.600 | 28.258 | 23.681 | 1.00 | 15.45 | C |
| ATOM | 3360 | CE2 | TYR | X 436 | 29.480 | 27.319 | 21.464 | 1.00 | 15.42 | C |
| ATOM | 3361 | CZ  | TYR | X 436 | 29.968 | 27.279 | 22.763 | 1.00 | 18.79 | C |
| ATOM | 3362 | OH  | TYR | X 436 | 30.827 | 26.263 | 23.132 | 1.00 | 21.48 | O |
| ATOM | 3621 | N   | ASP | F 1   | 28.847 | 41.426 | 24.951 | 1.00 | 34.85 | N |
| ATOM | 3622 | CA  | ASP | F 1   | 29.773 | 40.372 | 25.482 | 1.00 | 34.05 | C |
| ATOM | 3623 | C   | ASP | F 1   | 30.000 | 39.378 | 24.352 | 1.00 | 33.05 | C |

Figure 2A

| ATOM | 3624 | O | ASP | F | 1 | 29.348 | 39.478 | 23.319 | 1.00 | 35.27 | O |
|---|---|---|---|---|---|---|---|---|---|---|---|
| ATOM | 3625 | CB | ASP | F | 1 | 29.171 | 39.674 | 26.712 | 1.00 | 34.66 | C |
| ATOM | 3626 | CG | ASP | F | 1 | 27.813 | 39.049 | 26.435 | 1.00 | 36.33 | C |
| ATOM | 3627 | OD1 | ASP | F | 1 | 27.520 | 37.973 | 27.003 | 1.00 | 37.16 | O |
| ATOM | 3628 | OD2 | ASP | F | 1 | 27.022 | 39.637 | 25.670 | 1.00 | 39.41 | O |
| ATOM | 3629 | N | CYS | F | 2 | 30.891 | 38.414 | 24.550 | 1.00 | 31.11 | N |
| ATOM | 3630 | CA | CYS | F | 2 | 31.197 | 37.448 | 23.503 | 1.00 | 28.39 | C |
| ATOM | 3631 | C | CYS | F | 2 | 31.028 | 36.004 | 23.926 | 1.00 | 28.75 | C |
| ATOM | 3632 | O | CYS | F | 2 | 30.893 | 35.707 | 25.115 | 1.00 | 30.10 | O |
| ATOM | 3633 | CB | CYS | F | 2 | 32.630 | 37.646 | 23.006 | 1.00 | 27.54 | C |
| ATOM | 3634 | SG | CYS | F | 2 | 33.023 | 39.335 | 22.461 | 1.00 | 21.72 | S |
| ATOM | 3635 | N | ALA | F | 3 | 31.058 | 35.113 | 22.935 | 1.00 | 29.17 | N |
| ATOM | 3636 | CA | ALA | F | 3 | 30.931 | 33.670 | 23.139 | 1.00 | 30.01 | C |
| ATOM | 3637 | C | ALA | F | 3 | 32.111 | 33.026 | 22.437 | 1.00 | 30.25 | C |
| ATOM | 3638 | O | ALA | F | 3 | 32.504 | 33.462 | 21.354 | 1.00 | 30.98 | O |
| ATOM | 3639 | CB | ALA | F | 3 | 29.615 | 33.151 | 22.547 | 1.00 | 29.87 | C |
| ATOM | 3640 | N | ALA | F | 4 | 32.678 | 31.996 | 23.048 | 1.00 | 31.67 | N |
| ATOM | 3641 | CA | ALA | F | 4 | 33.834 | 31.325 | 22.474 | 1.00 | 32.06 | C |
| ATOM | 3642 | C | ALA | F | 4 | 33.608 | 29.818 | 22.440 | 1.00 | 32.05 | C |
| ATOM | 3643 | O | ALA | F | 4 | 33.087 | 29.237 | 23.390 | 1.00 | 32.14 | O |
| ATOM | 3644 | CB | ALA | F | 4 | 35.090 | 31.640 | 23.301 | 1.00 | 34.09 | C |
| ATOM | 3654 | N | HIS | F | 5 | 33.979 | 29.200 | 21.325 | 1.00 | 32.99 | N |
| ATOM | 3655 | CA | HIS | F | 5 | 33.846 | 27.763 | 21.136 | 1.00 | 32.73 | C |
| ATOM | 3656 | C | HIS | F | 5 | 35.259 | 27.206 | 21.000 | 1.00 | 34.20 | C |
| ATOM | 3657 | O | HIS | F | 5 | 35.922 | 27.419 | 19.978 | 1.00 | 34.53 | O |
| ATOM | 3658 | CB | HIS | F | 5 | 33.029 | 27.464 | 19.863 | 1.00 | 33.09 | C |
| ATOM | 3659 | CG | HIS | F | 5 | 32.839 | 26.000 | 19.580 | 1.00 | 32.96 | C |
| ATOM | 3660 | ND1 | HIS | F | 5 | 32.280 | 25.128 | 20.492 | 1.00 | 31.19 | N |
| ATOM | 3661 | CD2 | HIS | F | 5 | 33.144 | 25.255 | 18.489 | 1.00 | 31.40 | C |
| ATOM | 3662 | CE1 | HIS | F | 5 | 32.253 | 23.911 | 19.978 | 1.00 | 30.26 | C |
| ATOM | 3663 | NE2 | HIS | F | 5 | 32.772 | 23.962 | 18.764 | 1.00 | 30.80 | N |
| ATOM | 3664 | N | LEU | F | 6 | 35.731 | 26.537 | 22.050 | 1.00 | 34.57 | N |
| ATOM | 3665 | CA | LEU | F | 6 | 37.067 | 25.944 | 22.052 | 1.00 | 35.43 | C |
| ATOM | 3666 | C | LEU | F | 6 | 38.148 | 26.986 | 21.761 | 1.00 | 36.60 | C |
| ATOM | 3667 | O | LEU | F | 6 | 39.099 | 26.723 | 21.015 | 1.00 | 35.70 | O |
| ATOM | 3668 | CB | LEU | F | 6 | 37.155 | 24.821 | 21.008 | 1.00 | 35.00 | C |
| ATOM | 3669 | CG | LEU | F | 6 | 36.178 | 23.651 | 21.094 | 1.00 | 34.12 | C |
| ATOM | 3670 | CD1 | LEU | F | 6 | 36.327 | 22.767 | 19.848 | 1.00 | 34.64 | C |
| ATOM | 3671 | CD2 | LEU | F | 6 | 36.428 | 22.872 | 22.372 | 1.00 | 33.53 | C |
| ATOM | 3672 | N | GLY | F | 7 | 37.991 | 28.175 | 22.334 | 1.00 | 37.43 | N |
| ATOM | 3673 | CA | GLY | F | 7 | 38.969 | 29.223 | 22.114 | 1.00 | 38.95 | C |
| ATOM | 3674 | C | GLY | F | 7 | 38.664 | 30.140 | 20.942 | 1.00 | 39.28 | C |
| ATOM | 3675 | O | GLY | F | 7 | 39.090 | 31.292 | 20.945 | 1.00 | 42.00 | O |
| ATOM | 3676 | N | GLU | F | 8 | 37.936 | 29.648 | 19.943 | 1.00 | 38.59 | N |
| ATOM | 3677 | CA | GLU | F | 8 | 37.590 | 30.458 | 18.773 | 1.00 | 37.57 | C |
| ATOM | 3678 | C | GLU | F | 8 | 36.463 | 31.440 | 19.058 | 1.00 | 34.89 | C |
| ATOM | 3679 | O | GLU | F | 8 | 35.497 | 31.099 | 19.742 | 1.00 | 34.71 | O |
| ATOM | 3680 | CB | GLU | F | 8 | 37.165 | 29.568 | 17.615 | 1.00 | 41.42 | C |
| ATOM | 3681 | CG | GLU | F | 8 | 38.262 | 29.147 | 16.676 | 1.00 | 45.84 | C |
| ATOM | 3682 | CD | GLU | F | 8 | 37.713 | 28.301 | 15.550 | 1.00 | 50.27 | C |
| ATOM | 3683 | OE1 | GLU | F | 8 | 37.431 | 28.858 | 14.459 | 1.00 | 50.07 | O |
| ATOM | 3684 | OE2 | GLU | F | 8 | 37.531 | 27.084 | 15.780 | 1.00 | 52.26 | O |

Figure 2A

| | | | | | | | | | | | |
|---|---|---|---|---|---|---|---|---|---|---|---|
| ATOM | 3685 | N | LEU | F | 9 | 36.569 | 32.648 | 18.511 | 1.00 | 32.00 | N |
| ATOM | 3686 | CA | LEU | F | 9 | 35.535 | 33.658 | 18.721 | 1.00 | 27.85 | C |
| ATOM | 3687 | C | LEU | F | 9 | 34.328 | 33.315 | 17.880 | 1.00 | 25.43 | C |
| ATOM | 3688 | O | LEU | F | 9 | 34.435 | 33.119 | 16.671 | 1.00 | 26.38 | O |
| ATOM | 3689 | CB | LEU | F | 9 | 36.023 | 35.065 | 18.351 | 1.00 | 28.29 | C |
| ATOM | 3690 | CG | LEU | F | 9 | 34.985 | 36.179 | 18.579 | 1.00 | 27.64 | C |
| ATOM | 3691 | CD1 | LEU | F | 9 | 34.647 | 36.290 | 20.072 | 1.00 | 26.13 | C |
| ATOM | 3692 | CD2 | LEU | F | 9 | 35.479 | 37.503 | 18.045 | 1.00 | 25.10 | C |
| ATOM | 3693 | N | VAL | F | 10 | 33.179 | 33.227 | 18.532 | 1.00 | 22.45 | N |
| ATOM | 3694 | CA | VAL | F | 10 | 31.948 | 32.911 | 17.844 | 1.00 | 18.45 | C |
| ATOM | 3695 | C | VAL | F | 10 | 31.253 | 34.185 | 17.426 | 1.00 | 18.93 | C |
| ATOM | 3696 | O | VAL | F | 10 | 31.153 | 34.473 | 16.238 | 1.00 | 19.89 | O |
| ATOM | 3697 | CB | VAL | F | 10 | 30.992 | 32.076 | 18.726 | 1.00 | 16.56 | C |
| ATOM | 3698 | CG1 | VAL | F | 10 | 29.665 | 31.886 | 18.029 | 1.00 | 16.45 | C |
| ATOM | 3699 | CG2 | VAL | F | 10 | 31.592 | 30.723 | 19.004 | 1.00 | 16.04 | C |
| ATOM | 3700 | N | TRP | F | 11 | 30.844 | 34.989 | 18.399 | 1.00 | 18.72 | N |
| ATOM | 3701 | CA | TRP | F | 11 | 30.109 | 36.207 | 18.093 | 1.00 | 19.89 | C |
| ATOM | 3702 | C | TRP | F | 11 | 30.086 | 37.109 | 19.310 | 1.00 | 22.86 | C |
| ATOM | 3703 | O | TRP | F | 11 | 30.247 | 36.626 | 20.437 | 1.00 | 23.85 | O |
| ATOM | 3704 | CB | TRP | F | 11 | 28.667 | 35.819 | 17.763 | 1.00 | 16.70 | C |
| ATOM | 3705 | CG | TRP | F | 11 | 27.886 | 36.841 | 17.024 | 1.00 | 15.87 | C |
| ATOM | 3706 | CD1 | TRP | F | 11 | 27.014 | 37.759 | 17.553 | 1.00 | 16.27 | C |
| ATOM | 3707 | CD2 | TRP | F | 11 | 27.862 | 37.034 | 15.608 | 1.00 | 16.46 | C |
| ATOM | 3708 | NE1 | TRP | F | 11 | 26.449 | 38.510 | 16.547 | 1.00 | 15.16 | N |
| ATOM | 3709 | CE2 | TRP | F | 11 | 26.954 | 38.088 | 15.343 | 1.00 | 17.92 | C |
| ATOM | 3710 | CE3 | TRP | F | 11 | 28.517 | 36.415 | 14.533 | 1.00 | 17.45 | C |
| ATOM | 3711 | CZ2 | TRP | F | 11 | 26.688 | 38.538 | 14.041 | 1.00 | 15.75 | C |
| ATOM | 3712 | CZ3 | TRP | F | 11 | 28.249 | 36.861 | 13.240 | 1.00 | 13.24 | C |
| ATOM | 3713 | CH2 | TRP | F | 11 | 27.343 | 37.912 | 13.008 | 1.00 | 14.35 | C |
| ATOM | 3714 | N | CYS | F | 12 | 29.859 | 38.403 | 19.088 | 1.00 | 24.42 | N |
| ATOM | 3715 | CA | CYS | F | 12 | 29.775 | 39.365 | 20.181 | 1.00 | 26.86 | C |
| ATOM | 3716 | C | CYS | F | 12 | 28.615 | 40.322 | 19.943 | 1.00 | 29.15 | C |
| ATOM | 3717 | O | CYS | F | 12 | 28.449 | 40.828 | 18.830 | 1.00 | 27.79 | O |
| ATOM | 3718 | CB | CYS | F | 12 | 31.055 | 40.198 | 20.294 | 1.00 | 25.49 | C |
| ATOM | 3719 | SG | CYS | F | 12 | 32.631 | 39.306 | 20.465 | 1.00 | 27.47 | S |
| ATOM | 3720 | N | THR | F | 13 | 27.789 | 40.533 | 20.963 | 1.00 | 32.63 | N |
| ATOM | 3721 | CA | THR | F | 13 | 26.689 | 41.481 | 20.838 | 1.00 | 38.91 | C |
| ATOM | 3722 | C | THR | F | 13 | 27.201 | 42.868 | 21.245 | 1.00 | 41.56 | C |
| ATOM | 3723 | O | THR | F | 13 | 27.732 | 43.056 | 22.363 | 1.00 | 42.26 | O |
| ATOM | 3724 | CB | THR | F | 13 | 25.443 | 41.110 | 21.712 | 1.00 | 40.71 | C |
| ATOM | 3725 | OG1 | THR | F | 13 | 25.805 | 41.012 | 23.101 | 1.00 | 39.07 | O |
| ATOM | 3726 | CG2 | THR | F | 13 | 24.800 | 39.810 | 21.202 | 1.00 | 39.18 | C |
| HETATM | 3727 | N | NH2 | F | 14 | 27.091 | 43.827 | 20.331 | 1.00 | 40.27 | N |
| TER | 3728 | | NH2 | F | 14 | | | | | | |

Figure 2B

| | | | | | | | | | |
|---|---|---|---|---|---|---|---|---|---|
| ATOM | 1495 | N | SER | D 424 | 1.722 | 20.062 | 14.486 | 1.00 | 23.86 | N |
| ATOM | 1496 | CA | SER | D 424 | 3.071 | 19.631 | 14.159 | 1.00 | 23.86 | C |
| ATOM | 1497 | C | SER | D 424 | 3.136 | 18.213 | 13.611 | 1.00 | 23.86 | C |
| ATOM | 1498 | O | SER | D 424 | 2.443 | 17.317 | 14.104 | 1.00 | 23.86 | O |
| ATOM | 1499 | CB | SER | D 424 | 3.965 | 19.744 | 15.398 | 1.00 | 23.86 | C |
| ATOM | 1500 | OG | SER | D 424 | 3.863 | 21.025 | 15.993 | 1.00 | 23.86 | O |
| ATOM | 1501 | N | CYS | D 425 | 3.963 | 18.023 | 12.585 | 1.00 | 4.89 | N |
| ATOM | 1502 | CA | CYS | D 425 | 4.157 | 16.723 | 11.963 | 1.00 | 4.89 | C |
| ATOM | 1503 | C | CYS | D 425 | 5.447 | 16.167 | 12.533 | 1.00 | 4.89 | C |
| ATOM | 1504 | O | CYS | D 425 | 6.526 | 16.663 | 12.223 | 1.00 | 4.89 | O |
| ATOM | 1505 | CB | CYS | D 425 | 4.290 | 16.865 | 10.449 | 1.00 | 4.89 | C |
| ATOM | 1506 | SG | CYS | D 425 | 4.514 | 15.266 | 9.604 | 1.00 | 4.89 | S |
| ATOM | 1507 | N | SER | D 426 | 5.331 | 15.171 | 13.400 | 1.00 | 12.94 | N |
| ATOM | 1508 | CA | SER | D 426 | 6.490 | 14.570 | 14.037 | 1.00 | 12.94 | C |
| ATOM | 1509 | C | SER | D 426 | 6.887 | 13.296 | 13.321 | 1.00 | 12.94 | C |
| ATOM | 1510 | O | SER | D 426 | 6.078 | 12.379 | 13.184 | 1.00 | 12.94 | O |
| ATOM | 1511 | CB | SER | D 426 | 6.178 | 14.253 | 15.502 | 1.00 | 12.94 | C |
| ATOM | 1512 | OG | SER | D 426 | 5.520 | 15.341 | 16.138 | 1.00 | 12.94 | O |
| ATOM | 1513 | N | VAL | D 427 | 8.126 | 13.236 | 12.859 | 1.00 | 2.00 | N |
| ATOM | 1514 | CA | VAL | D 427 | 8.611 | 12.054 | 12.170 | 1.00 | 2.00 | C |
| ATOM | 1515 | C | VAL | D 427 | 9.854 | 11.464 | 12.837 | 1.00 | 2.00 | C |
| ATOM | 1516 | O | VAL | D 427 | 10.759 | 12.186 | 13.267 | 1.00 | 2.00 | O |
| ATOM | 1517 | CB | VAL | D 427 | 8.861 | 12.336 | 10.672 | 1.00 | 2.00 | C |
| ATOM | 1518 | CG1 | VAL | D 427 | 9.709 | 13.553 | 10.507 | 1.00 | 2.00 | C |
| ATOM | 1519 | CG2 | VAL | D 427 | 9.511 | 11.150 | 10.005 | 1.00 | 2.00 | C |
| ATOM | 1520 | N | MET | D 428 | 9.841 | 10.146 | 12.984 | 1.00 | 12.84 | N |
| ATOM | 1521 | CA | MET | D 428 | 10.936 | 9.405 | 13.583 | 1.00 | 12.84 | C |
| ATOM | 1522 | C | MET | D 428 | 11.537 | 8.509 | 12.508 | 1.00 | 12.84 | C |
| ATOM | 1523 | O | MET | D 428 | 10.813 | 7.798 | 11.809 | 1.00 | 12.84 | O |
| ATOM | 1524 | CB | MET | D 428 | 10.424 | 8.538 | 14.739 | 1.00 | 12.84 | C |
| ATOM | 1525 | CG | MET | D 428 | 9.852 | 9.319 | 15.916 | 1.00 | 12.84 | C |
| ATOM | 1526 | SD | MET | D 428 | 9.537 | 8.258 | 17.346 | 1.00 | 12.84 | S |
| ATOM | 1527 | CE | MET | D 428 | 11.158 | 8.180 | 18.065 | 1.00 | 12.84 | C |
| ATOM | 1528 | N | HIS | D 429 | 12.853 | 8.572 | 12.349 | 1.00 | 17.82 | N |
| ATOM | 1529 | CA | HIS | D 429 | 13.535 | 7.751 | 11.361 | 1.00 | 17.82 | C |
| ATOM | 1530 | C | HIS | D 429 | 15.007 | 7.575 | 11.698 | 1.00 | 17.82 | C |
| ATOM | 1531 | O | HIS | D 429 | 15.679 | 8.509 | 12.140 | 1.00 | 17.82 | O |
| ATOM | 1532 | CB | HIS | D 429 | 13.379 | 8.335 | 9.947 | 1.00 | 17.82 | C |
| ATOM | 1533 | CG | HIS | D 429 | 13.993 | 7.489 | 8.873 | 1.00 | 17.82 | C |
| ATOM | 1534 | ND1 | HIS | D 429 | 13.480 | 6.264 | 8.501 | 1.00 | 17.82 | N |
| ATOM | 1535 | CD2 | HIS | D 429 | 15.093 | 7.682 | 8.107 | 1.00 | 17.82 | C |
| ATOM | 1536 | CE1 | HIS | D 429 | 14.236 | 5.739 | 7.555 | 1.00 | 17.82 | C |
| ATOM | 1537 | NE2 | HIS | D 429 | 15.223 | 6.580 | 7.297 | 1.00 | 17.82 | N |
| ATOM | 1538 | N | GLU | D 430 | 15.496 | 6.367 | 11.453 | 1.00 | 35.29 | N |
| ATOM | 1539 | CA | GLU | D 430 | 16.880 | 5.991 | 11.706 | 1.00 | 35.29 | C |
| ATOM | 1540 | C | GLU | D 430 | 17.935 | 7.050 | 11.385 | 1.00 | 35.29 | C |
| ATOM | 1541 | O | GLU | D 430 | 18.730 | 7.408 | 12.249 | 1.00 | 35.29 | O |
| ATOM | 1542 | CB | GLU | D 430 | 17.198 | 4.702 | 10.947 | 1.00 | 35.29 | C |
| ATOM | 1543 | CG | GLU | D 430 | 18.621 | 4.218 | 11.111 | 1.00 | 35.29 | C |
| ATOM | 1544 | CD | GLU | D 430 | 18.942 | 3.056 | 10.202 | 1.00 | 35.29 | C |
| ATOM | 1545 | OE1 | GLU | D 430 | 18.085 | 2.153 | 10.064 | 1.00 | 35.29 | O |
| ATOM | 1546 | OE2 | GLU | D 430 | 20.057 | 3.049 | 9.630 | 1.00 | 35.29 | O |
| ATOM | 1547 | N | ALA | D 431 | 17.925 | 7.563 | 10.158 | 1.00 | 2.00 | N |

Figure 2B

| ATOM | 1548 | CA  | ALA | D 431 | 18.909 | 8.551  | 9.726  | 1.00 | 2.00  | C |
|------|------|-----|-----|-------|--------|--------|--------|------|-------|---|
| ATOM | 1549 | C   | ALA | D 431 | 18.696 | 9.997  | 10.161 | 1.00 | 2.00  | C |
| ATOM | 1550 | O   | ALA | D 431 | 19.312 | 10.902 | 9.611  | 1.00 | 2.00  | O |
| ATOM | 1551 | CB  | ALA | D 431 | 19.082 | 8.488  | 8.229  | 1.00 | 2.00  | C |
| ATOM | 1552 | N   | LEU | D 432 | 17.819 | 10.229 | 11.126 | 1.00 | 2.68  | N |
| ATOM | 1553 | CA  | LEU | D 432 | 17.584 | 11.589 | 11.598 | 1.00 | 2.68  | C |
| ATOM | 1554 | C   | LEU | D 432 | 18.462 | 11.869 | 12.827 | 1.00 | 2.68  | C |
| ATOM | 1555 | O   | LEU | D 432 | 18.668 | 10.989 | 13.667 | 1.00 | 2.68  | O |
| ATOM | 1556 | CB  | LEU | D 432 | 16.104 | 11.785 | 11.941 | 1.00 | 2.68  | C |
| ATOM | 1557 | CG  | LEU | D 432 | 15.121 | 11.843 | 10.777 | 1.00 | 2.68  | C |
| ATOM | 1558 | CD1 | LEU | D 432 | 13.718 | 11.633 | 11.275 | 1.00 | 2.68  | C |
| ATOM | 1559 | CD2 | LEU | D 432 | 15.245 | 13.173 | 10.068 | 1.00 | 2.68  | C |
| ATOM | 1560 | N   | HIS | D 433 | 18.897 | 13.117 | 12.968 | 1.00 | 49.93 | N |
| ATOM | 1561 | CA  | HIS | D 433 | 19.757 | 13.533 | 14.076 | 1.00 | 49.93 | C |
| ATOM | 1562 | C   | HIS | D 433 | 19.526 | 12.874 | 15.436 | 1.00 | 49.93 | C |
| ATOM | 1563 | O   | HIS | D 433 | 20.476 | 12.454 | 16.086 | 1.00 | 49.93 | O |
| ATOM | 1564 | CB  | HIS | D 433 | 19.721 | 15.051 | 14.247 | 1.00 | 49.93 | C |
| ATOM | 1565 | CG  | HIS | D 433 | 20.489 | 15.539 | 15.439 | 1.00 | 49.93 | C |
| ATOM | 1566 | ND1 | HIS | D 433 | 21.793 | 15.167 | 15.689 | 1.00 | 49.93 | N |
| ATOM | 1567 | CD2 | HIS | D 433 | 20.130 | 16.354 | 16.459 | 1.00 | 49.93 | C |
| ATOM | 1568 | CE1 | HIS | D 433 | 22.201 | 15.726 | 16.810 | 1.00 | 49.93 | C |
| ATOM | 1569 | NE2 | HIS | D 433 | 21.213 | 16.452 | 17.299 | 1.00 | 49.93 | N |
| ATOM | 1570 | N   | ASN | D 434 | 18.284 | 12.852 | 15.896 | 1.00 | 2.00  | N |
| ATOM | 1571 | CA  | ASN | D 434 | 17.960 | 12.257 | 17.192 | 1.00 | 2.00  | C |
| ATOM | 1572 | C   | ASN | D 434 | 16.830 | 11.265 | 16.963 | 1.00 | 2.00  | C |
| ATOM | 1573 | O   | ASN | D 434 | 16.036 | 10.987 | 17.862 | 1.00 | 2.00  | O |
| ATOM | 1574 | CB  | ASN | D 434 | 17.541 | 13.371 | 18.175 | 1.00 | 2.00  | C |
| ATOM | 1575 | CG  | ASN | D 434 | 16.960 | 12.841 | 19.487 | 1.00 | 2.00  | C |
| ATOM | 1576 | OD1 | ASN | D 434 | 17.381 | 11.808 | 20.005 | 1.00 | 2.00  | O |
| ATOM | 1577 | ND2 | ASN | D 434 | 15.978 | 13.558 | 20.026 | 1.00 | 2.00  | N |
| ATOM | 1578 | N   | HIS | D 435 | 16.773 | 10.706 | 15.755 | 1.00 | 22.31 | N |
| ATOM | 1579 | CA  | HIS | D 435 | 15.713 | 9.768  | 15.393 | 1.00 | 22.31 | C |
| ATOM | 1580 | C   | HIS | D 435 | 14.368 | 10.477 | 15.540 | 1.00 | 22.31 | C |
| ATOM | 1581 | O   | HIS | D 435 | 13.333 | 9.827  | 15.668 | 1.00 | 22.31 | O |
| ATOM | 1582 | CB  | HIS | D 435 | 15.729 | 8.540  | 16.318 | 1.00 | 22.31 | C |
| ATOM | 1583 | CG  | HIS | D 435 | 16.910 | 7.645  | 16.123 | 1.00 | 22.31 | C |
| ATOM | 1584 | ND1 | HIS | D 435 | 16.920 | 6.330  | 16.534 | 1.00 | 22.31 | N |
| ATOM | 1585 | CD2 | HIS | D 435 | 18.104 | 7.863  | 15.529 | 1.00 | 22.31 | C |
| ATOM | 1586 | CE1 | HIS | D 435 | 18.070 | 5.773  | 16.198 | 1.00 | 22.31 | C |
| ATOM | 1587 | NE2 | HIS | D 435 | 18.806 | 6.683  | 15.587 | 1.00 | 22.31 | N |
| ATOM | 1588 | N   | TYR | D 436 | 14.389 | 11.806 | 15.471 | 1.00 | 2.00  | N |
| ATOM | 1589 | CA  | TYR | D 436 | 13.188 | 12.612 | 15.645 | 1.00 | 2.00  | C |
| ATOM | 1590 | C   | TYR | D 436 | 13.309 | 13.959 | 14.936 | 1.00 | 2.00  | C |
| ATOM | 1591 | O   | TYR | D 436 | 14.415 | 14.477 | 14.765 | 1.00 | 2.00  | O |
| ATOM | 1592 | CB  | TYR | D 436 | 12.963 | 12.869 | 17.149 | 1.00 | 2.00  | C |
| ATOM | 1593 | CG  | TYR | D 436 | 11.673 | 13.599 | 17.481 | 1.00 | 2.00  | C |
| ATOM | 1594 | CD1 | TYR | D 436 | 10.483 | 12.895 | 17.659 | 1.00 | 2.00  | C |
| ATOM | 1595 | CD2 | TYR | D 436 | 11.626 | 14.991 | 17.546 | 1.00 | 2.00  | C |
| ATOM | 1596 | CE1 | TYR | D 436 | 9.275  | 13.556 | 17.881 | 1.00 | 2.00  | C |
| ATOM | 1597 | CE2 | TYR | D 436 | 10.421 | 15.661 | 17.767 | 1.00 | 2.00  | C |
| ATOM | 1598 | CZ  | TYR | D 436 | 9.250  | 14.932 | 17.930 | 1.00 | 2.00  | C |
| ATOM | 1599 | OH  | TYR | D 436 | 8.048  | 15.578 | 18.105 | 1.00 | 2.00  | O |
| ATOM | 105  | N   | LEU | B 251 | 13.677 | 2.651  | 16.873 | 1.00 | 22.41 | N |

Figure 2B

| ATOM | 106 | CA | LEU | B 251 | 14.234 | 3.995 | 16.926 | 1.00 | 22.41 | C |
|---|---|---|---|---|---|---|---|---|---|---|
| ATOM | 107 | C | LEU | B 251 | 14.404 | 4.605 | 18.308 | 1.00 | 22.41 | C |
| ATOM | 108 | O | LEU | B 251 | 15.305 | 5.415 | 18.503 | 1.00 | 22.41 | O |
| ATOM | 109 | CB | LEU | B 251 | 13.434 | 4.929 | 16.027 | 1.00 | 22.41 | C |
| ATOM | 110 | CG | LEU | B 251 | 13.277 | 4.382 | 14.609 | 1.00 | 22.41 | C |
| ATOM | 111 | CD1 | LEU | B 251 | 12.423 | 5.319 | 13.785 | 1.00 | 22.41 | C |
| ATOM | 112 | CD2 | LEU | B 251 | 14.633 | 4.163 | 13.965 | 1.00 | 22.41 | C |
| ATOM | 113 | N | MET | B 252 | 13.522 | 4.276 | 19.248 | 1.00 | 25.23 | N |
| ATOM | 114 | CA | MET | B 252 | 13.656 | 4.814 | 20.603 | 1.00 | 25.23 | C |
| ATOM | 115 | C | MET | B 252 | 14.149 | 3.785 | 21.619 | 1.00 | 25.23 | C |
| ATOM | 116 | O | MET | B 252 | 13.500 | 2.767 | 21.863 | 1.00 | 25.23 | O |
| ATOM | 117 | CB | MET | B 252 | 12.379 | 5.523 | 21.072 | 1.00 | 25.23 | C |
| ATOM | 118 | CG | MET | B 252 | 11.063 | 4.898 | 20.662 | 1.00 | 25.23 | C |
| ATOM | 119 | SD | MET | B 252 | 9.777 | 6.180 | 20.565 | 1.00 | 25.23 | S |
| ATOM | 120 | CE | MET | B 252 | 9.364 | 6.399 | 22.280 | 1.00 | 25.23 | C |
| ATOM | 121 | N | ILE | B 253 | 15.313 | 4.074 | 22.197 | 1.00 | 23.63 | N |
| ATOM | 122 | CA | ILE | B 253 | 15.983 | 3.210 | 23.170 | 1.00 | 23.63 | C |
| ATOM | 123 | C | ILE | B 253 | 15.090 | 2.730 | 24.326 | 1.00 | 23.63 | C |
| ATOM | 124 | O | ILE | B 253 | 15.333 | 1.674 | 24.911 | 1.00 | 23.63 | O |
| ATOM | 125 | CB | ILE | B 253 | 17.258 | 3.917 | 23.732 | 1.00 | 23.63 | C |
| ATOM | 126 | CG1 | ILE | B 253 | 18.195 | 2.904 | 24.389 | 1.00 | 23.63 | C |
| ATOM | 127 | CG2 | ILE | B 253 | 16.886 | 5.019 | 24.710 | 1.00 | 23.63 | C |
| ATOM | 128 | CD1 | ILE | B 253 | 19.044 | 2.123 | 23.397 | 1.00 | 23.63 | C |
| ATOM | 129 | N | SER | B 254 | 14.044 | 3.495 | 24.618 | 1.00 | 34.09 | N |
| ATOM | 130 | CA | SER | B 254 | 13.118 | 3.174 | 25.697 | 1.00 | 34.09 | C |
| ATOM | 131 | C | SER | B 254 | 12.168 | 2.006 | 25.423 | 1.00 | 34.09 | C |
| ATOM | 132 | O | SER | B 254 | 11.650 | 1.390 | 26.356 | 1.00 | 34.09 | O |
| ATOM | 133 | CB | SER | B 254 | 12.321 | 4.424 | 26.069 | 1.00 | 34.09 | C |
| ATOM | 134 | OG | SER | B 254 | 11.935 | 5.147 | 24.909 | 1.00 | 34.09 | O |
| ATOM | 135 | N | ARG | B 255 | 11.936 | 1.711 | 24.148 | 1.00 | 23.81 | N |
| ATOM | 136 | CA | ARG | B 255 | 11.042 | 0.623 | 23.762 | 1.00 | 23.81 | C |
| ATOM | 137 | C | ARG | B 255 | 11.824 | -0.665 | 23.532 | 1.00 | 23.81 | C |
| ATOM | 138 | O | ARG | B 255 | 13.049 | -0.641 | 23.372 | 1.00 | 23.81 | O |
| ATOM | 139 | CB | ARG | B 255 | 10.276 | 1.002 | 22.491 | 1.00 | 23.81 | C |
| ATOM | 140 | CG | ARG | B 255 | 9.483 | 2.302 | 22.594 | 1.00 | 23.81 | C |
| ATOM | 141 | CD | ARG | B 255 | 8.405 | 2.208 | 23.662 | 1.00 | 23.81 | C |
| ATOM | 142 | NE | ARG | B 255 | 7.643 | 3.446 | 23.815 | 1.00 | 23.81 | N |
| ATOM | 143 | CZ | ARG | B 255 | 6.796 | 3.918 | 22.907 | 1.00 | 23.81 | C |
| ATOM | 144 | NH1 | ARG | B 255 | 6.601 | 3.264 | 21.770 | 1.00 | 23.81 | N |
| ATOM | 145 | NH2 | ARG | B 255 | 6.106 | 5.023 | 23.156 | 1.00 | 23.81 | N |
| ATOM | 4018 | N | ARG | E 96 | 14.003 | 15.127 | 25.869 | 1.00 | 16.08 | N |
| ATOM | 4019 | CA | ARG | E 96 | 13.379 | 14.548 | 24.691 | 1.00 | 16.08 | C |
| ATOM | 4020 | C | ARG | E 96 | 14.482 | 13.998 | 23.806 | 1.00 | 16.08 | C |
| ATOM | 4021 | O | ARG | E 96 | 14.952 | 14.674 | 22.891 | 1.00 | 16.08 | O |
| ATOM | 4022 | CB | ARG | E 96 | 12.566 | 15.607 | 23.939 | 1.00 | 16.08 | C |
| ATOM | 4023 | CG | ARG | E 96 | 11.573 | 15.031 | 22.949 | 1.00 | 16.08 | C |
| ATOM | 4024 | CD | ARG | E 96 | 11.919 | 15.433 | 21.540 | 1.00 | 16.08 | C |
| ATOM | 4025 | NE | ARG | E 96 | 11.849 | 16.877 | 21.330 | 1.00 | 16.08 | N |
| ATOM | 4026 | CZ | ARG | E 96 | 10.728 | 17.548 | 21.096 | 1.00 | 16.08 | C |
| ATOM | 4027 | NH1 | ARG | E 96 | 9.566 | 16.912 | 21.051 | 1.00 | 16.08 | N |
| ATOM | 4028 | NH2 | ARG | E 96 | 10.779 | 18.848 | 20.864 | 1.00 | 16.08 | N |
| ATOM | 4029 | N | SER | E 97 | 14.906 | 12.776 | 24.103 | 1.00 | 24.55 | N |
| ATOM | 4030 | CA | SER | E 97 | 15.968 | 12.120 | 23.352 | 1.00 | 24.55 | C |

Figure 2B

| | | | | | | | | | |
|---|---|---|---|---|---|---|---|---|---|
| ATOM | 4031 | C | SER | E 97 | 15.717 | 10.621 | 23.256 | 1.00 | 24.55 | C |
| ATOM | 4032 | O | SER | E 97 | 15.240 | 10.001 | 24.209 | 1.00 | 24.55 | O |
| ATOM | 4033 | CB | SER | E 97 | 17.304 | 12.381 | 24.033 | 1.00 | 24.55 | C |
| ATOM | 4034 | OG | SER | E 97 | 17.215 | 12.074 | 25.413 | 1.00 | 24.55 | O |
| ATOM | 4035 | N | TYR | E 98 | 16.057 | 10.043 | 22.108 | 1.00 | 2.00 | N |
| ATOM | 4036 | CA | TYR | E 98 | 15.856 | 8.615 | 21.863 | 1.00 | 2.00 | C |
| ATOM | 4037 | C | TYR | E 98 | 17.175 | 7.887 | 21.594 | 1.00 | 2.00 | C |
| ATOM | 4038 | O | TYR | E 98 | 17.313 | 6.695 | 21.883 | 1.00 | 2.00 | O |
| ATOM | 4039 | CB | TYR | E 98 | 14.893 | 8.442 | 20.690 | 1.00 | 2.00 | C |
| ATOM | 4040 | CG | TYR | E 98 | 13.685 | 9.344 | 20.810 | 1.00 | 2.00 | C |
| ATOM | 4041 | CD1 | TYR | E 98 | 12.555 | 8.939 | 21.523 | 1.00 | 2.00 | C |
| ATOM | 4042 | CD2 | TYR | E 98 | 13.687 | 10.622 | 20.247 | 1.00 | 2.00 | C |
| ATOM | 4043 | CE1 | TYR | E 98 | 11.461 | 9.783 | 21.676 | 1.00 | 2.00 | C |
| ATOM | 4044 | CE2 | TYR | E 98 | 12.596 | 11.474 | 20.395 | 1.00 | 2.00 | C |
| ATOM | 4045 | CZ | TYR | E 98 | 11.489 | 11.047 | 21.111 | 1.00 | 2.00 | C |
| ATOM | 4046 | OH | TYR | E 98 | 10.414 | 11.884 | 21.269 | 1.00 | 2.00 | O |
| ATOM | 4047 | N | VAL | E 99 | 18.140 | 8.608 | 21.033 | 1.00 | 19.77 | N |
| ATOM | 4048 | CA | VAL | E 99 | 19.444 | 8.033 | 20.743 | 1.00 | 19.77 | C |
| ATOM | 4049 | C | VAL | E 99 | 20.170 | 7.703 | 22.043 | 1.00 | 19.77 | C |
| ATOM | 4050 | O | VAL | E 99 | 20.021 | 8.405 | 23.045 | 1.00 | 19.77 | O |
| ATOM | 4051 | CB | VAL | E 99 | 20.317 | 8.991 | 19.898 | 1.00 | 19.77 | C |
| ATOM | 4052 | CG1 | VAL | E 99 | 19.796 | 9.069 | 18.474 | 1.00 | 19.77 | C |
| ATOM | 4053 | CG2 | VAL | E 99 | 20.331 | 10.375 | 20.517 | 1.00 | 19.77 | C |

INHIBITION OF IMMUNE COMPLEX FORMATION

CROSS-REFERENCE TO RELATED APPLICATIONS

This application is a continuation of U.S. Ser. No. 10/131,589, filed Apr. 24, 2002 now U.S. Pat. No. 6,916,904.

TECHNICAL FIELD

This invention relates to immune complex formation, and more particularly to the inhibition of immune complex formation by polypeptides and other small molecules.

BACKGROUND

Humoral immune responses are triggered when an antigen binds specifically to an antibody. The combination of an antibody molecule and an antigen forms a small, relatively soluble immune complex. Antigens either can be foreign substances, such as viral or bacterial polypeptides, or can be "self-antigens" such as polypeptides normally found in the human body. The immune system normally distinguishes foreign antigens from self-antigens. "Autoimmune" disease can occur, however, when this system breaks down, such that the immune system turns upon the body and destroys tissues or organ systems as if they were foreign substances. Examples of this process include the destruction of joints in rheumatoid arthritis (RA) and the destruction of the kidneys in lupus nephritis. Larger immune complexes are more pathogenic than small, more soluble immune complexes. The formation of large, relatively insoluble immune complexes can result from both the interaction of antibody molecules with antigen and the interaction of antibody molecules with each other. Such immune complexes also can result from interactions between antibodies in the absence of antigen.

Antibodies can prevent infections by coating viruses or bacteria, but otherwise are relatively harmless by themselves. In contrast, organ specific tissue damage can occur when antibodies combine with antigens and the resulting immune complexes bind to certain effector molecules in the body. Effector molecules are so named because they carry out the pathogenic effects of immune complexes. By inhibiting the formation of large, insoluble immune complexes, or by inhibiting the binding of immune complexes to effector molecules, the tissue damaging effects of immune complexes could be prevented.

SUMMARY

This invention is based on the discovery that a polypeptide having the amino acid sequence of SEQ ID NO:1, and related polypeptides and other compounds, can bind specifically and with high affinity to the $C_H2$-$C_H3$ domain of an immunoglobulin molecule, thus inhibiting the formation of insoluble immune complexes containing antibodies and antigens, and preventing the binding of such complexes to effector molecules.

The invention features a purified polypeptide that has the amino acid sequence $Xaa_1$-Cys-Ala-$Xaa_2$-His-$Xaa_3$-$Xaa_4$-$Xaa_5$-Leu-Val-Trp-Cys-$Xaa_6$. $Xaa_1$ can be absent or any amino acid (e.g., Arg or Pro), $Xaa_2$ can be any amino acid other than Trp, Phe, Tyr, or Ala (e.g., Aug), $Xaa_3$ can be any amino acid (e.g., Leu), $Xaa_4$ can be Gly or Ala, $Xaa_5$ can be Glu or Ala, and $Xaa_6$ can be absent or any non-aromatic amino acid (e.g., Thr). In one embodiment, $Xaa_1$ is Arg, $Xaa_2$ is Arg, $Xaa_3$ is Leu, $Xaa_4$ is Gly, $Xaa_5$ is Glu, and $Xaa_6$ is Thr. The purified polypeptide can have a binding affinity of at least 1 µM (e.g., at least 100 nM or at least 10 nM) for the $C_H2$-$C_H3$ cleft of an immunoglobulin molecule having at least one bound antigen. The amino-terminal amino acid of the polypeptide can be acetylated, and the carboxy-terminal amino acid of the polypeptide can be amidated. All amino acids of the polypeptide can be L-amino acids and all amino acids of the polypeptide can be natural amino acids. Alternatively, at least one amino acid of the polypeptide can be a D-amino acid, at least one amino acid of the polypeptide can be an unnatural amino acid, or at least one amino acid of the polypeptide can be an amino acid analog.

The polypeptide can be capable of inhibiting the Fc-mediated formation of an immune complex. The purified polypeptide can be capable of inhibiting the binding of rheumatoid factors, histones, FcR, myelin basic protein, pso p27, and C1q to the $C_H2$-$C_H3$ cleft of an immunoglobulin molecule. The immunoglobulin molecule can be bound by antigen.

The invention also features a purified polypeptide that is a retro-inverso isomer of the claimed polypeptide.

In another aspect, the invention features an isolated nucleic acid encoding the polypeptide of the invention.

In another aspect, the invention features a purified polypeptide having the amino acid sequence Cys-Ala-$Xaa_1$-His-$Xaa_2$-$Xaa_3$-$Xaa_4$-Leu-Val-Trp-Cys. $Xaa_1$ can be any amino acid other than Trp, Phe, Tyr, or Ala, $Xaa_2$ can be any amino acid, $Xaa_3$ can be Gly or Ala, and $Xaa_4$ can be Glu or Ala. The purified polypeptide can include a stabilizing group (e.g., an alanine at the amino terminus or an Ala-Pro-Pro sequence at the amino terminus). When the polypeptide is bound to the $C_H2$-$C_H3$ cleft of an immunoglobulin molecule, the polypeptide does not detectably bind to another biological molecule (e.g., another biological molecule having a $C_H2$-$C_H3$ cleft). The purified polypeptide typically is not more than 50 amino acids in length (e.g., not more than 30 amino acids in length or not more than 20 amino acids in length).

In yet another aspect, the invention features a compound having specific binding affinity for the $C_H2$-$C_H3$ cleft of an immunoglobulin molecule. The compound can interact in a monomeric fashion with the $C_H2$-$C_H3$ cleft through the amino acids at positions-252, 253, 435, and 436. The compound can have a binding affinity of at least 1 µM (e.g., at least 100 nM or at least 10 nM) for the $C_H2$-$C_H3$ cleft. The compound can be capable of acting as an inhibitor of Fc-mediated immune complex formation. The immunoglobulin molecule can be bound by antigen. The binding affinity can be at least 10-fold higher (e.g., at least 100-fold higher or at least 1000-fold higher) for an immunoglobulin molecule having bound antigen than for a monomeric immunoglobulin molecule.

In another aspect, the invention features a method of designing a ligand having specific binding affinity for the $C_H2$-$C_H3$ cleft of an immunoglobulin molecule having bound antigen. The method can involve (a) providing data containing the atomic coordinates of the amino acid residues at positions 252, 253, 435, and 436 within the $C_H2$-$C_H3$ cleft to a computer having a computer program capable of generating an atomic model of a molecule from the atomic coordinate data; (b) generating with the computer an atomic model of the $C_H2$-$C_H3$ cleft; (c) providing to the computer data containing the atomic coordinates of a candidate compound; (d) generating with the computer an atomic model of the candidate compound optimally positioned in the $C_H2$-$C_H3$ cleft; (e) determining whether the optimally positioned candidate compound interacts with the amino acid residues within the $C_H2$-$C_H3$ cleft; and (f) identifying the candidate compound as a ligand having specific binding affinity for the $C_H2$-$C_H3$ cleft if the candidate compound interacts with the amino acid residues. The atomic coordinates can be those provided in FIG. 2A or FIG. 2B. The ligand can have a binding affinity of at least 1 µM (e.g., at least 100 nM or at least 10 nM) for the $C_H2$-$C_H3$ cleft. The ligand typically does not detectably bind to another biological molecule (e.g., another biological molecule having a $C_H2$-$C_H3$ cleft) when bound to the $C_H2$-$C_H3$ cleft.

The ligand can be capable of inhibiting the Fc-mediated formation of an immune complex. The ligand can be capable of inhibiting the binding of rheumatoid factors, histones, FcR, C1q, and myelin basic protein to the $C_H2$-$C_H3$ cleft. The ligand can be capable of inhibiting the binding of pso p27 to the $C_H2$-$C_H3$ cleft, a rheumatoid factor, or other autoantibodies. The ligand can be a polypeptide that is 11 to 50 amino acids in length. The data of step (a) can further include the atomic coordinates of one or more other amino acid residues. The atomic coordinates of the other amino acid residues can be provided in FIG. 2A or FIG. 2B.

In another aspect, the invention features a method of designing a ligand having specific binding affinity for the $C_H2$-$C_H3$ cleft of an immunoglobulin molecule having bound antigen. The method can involve (a) providing to a computer data containing the atomic coordinates of a candidate compound, wherein the computer has stored in memory thereon an atomic model of the $CH_2$-$CH_3$ cleft, and wherein the model incorporates the atomic coordinates of the amino acid residues at positions 252, 253, 435, and 436 of the immunoglobulin molecule; (b) generating with the computer an atomic model of the candidate compound optimally positioned in the $C_H2$-$C_H3$ cleft; (c) determining whether the optimally positioned candidate compound interacts with the amino acid residues within the $C_H2$-$C_H3$ cleft; and (d) identifying the candidate compound as a ligand having specific binding affinity for the $C_H2$-$C_H3$ cleft if the candidate compound interacts with the amino acid residues. The atomic coordinates of the immunoglobulin molecule can be provided in FIG. 2A or FIG. 2B.

In yet another aspect, the invention features a method of identifying a compound capable of inhibiting immune complex formation. The method can involve (a) providing a computer having stored in memory thereon an atomic structural model of the $C_H2$-$C_H3$ cleft of an immunoglobulin molecule having bound antigen; (b) modeling a plurality of test compounds that fit spatially and preferentially into the $C_H2$-$C_H3$ cleft; and (c) screening the plurality of test compounds for immune complex formation, wherein a compound is identified if immune complex formation is inhibited. The atomic structural model can be generated using data from FIG. 2A or FIG. 2B. The compound can have a binding affinity of at least 1 μM (e.g., at least 100 nM or at least 10 nM) for the $C_H2$-$C_H3$ cleft.

In another aspect, the invention features a composition capable of inhibiting Fc-mediated immune complex formation, wherein the composition contains the purified polypeptide of the invention. The invention also features a composition capable of inhibiting Fc-mediated immune complex formation, wherein the composition contains the compound of the invention.

In yet another aspect, the invention features a method of inhibiting immune complex formation in a subject. The method can involve administering to the subject a composition of the invention. The administering can be by an inhaler, by a transdermal device (e.g., an iontophoretic device), or by injection. The subject can have rheumatoid arthritis, systemic lupus erythematosus, lupus nephritis, another autoimmune glomerulonephritis, atherosclerosis, multiple sclerosis, Parkinson's disease, psoriasis, ankylosing spondylitis, Crohn's disease, or cancer. The subject can be a transplant recipient.

In another aspect, the invention features a nebulizer (e.g., an inhaler or a nasal spray device) containing the purified polypeptide of the invention.

In another aspect, the invention features a method of treating rheumatoid arthritis. The method can involve inhibiting the binding of rheumatoid factors to immune complexes. The invention features a method of treating systemic lupus erythematosus, wherein the method can involve inhibiting the binding of histones to immune complexes. The invention features a method of treating an autoimmune disease, wherein the method can involve inhibiting the binding of Fc receptors to immune complexes. The invention also features a method of treating multiple sclerosis, wherein the method can involve inhibiting the binding of myelin basic protein to immune complexes. The invention features a method of treating cancer metastasis, wherein the method can involve inhibiting the binding of cancer cells to Fc receptors. The invention also features a method of decreasing the half-life of pathogenic immune complexes, wherein the method can involve inhibiting the binding of FcRn to immune complexes. The inhibiting in these methods can be achieved by administering the polypeptide, compound, or composition of the invention.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A and 1B are three-dimensional, computer-generated structural models of the $C_H2$-$C_H3$ cleft of an IgG molecule, showing the conformation of the cleft when the IgG is in an Fc-mediated immune complex or is non-immune complexed, as indicated.

FIG. 2A is a listing of atomic coordinates for an IgG molecule bound to a peptide ligand through the $C_H2$-$C_H3$ cleft. FIG. 2B is a listing of atomic coordinates for an IgG molecule bound to rheumatoid factor through the $C_H2$-$C_H3$ cleft.

FIG. 3 is a three-dimensional, computer-generated structural model of an IgG Fc $C_H2$-$C_H3$ cleft bound to a polypeptide having the amino acid sequence set forth in SEQ ID NO:2.

DETAILED DESCRIPTION

The invention provides polypeptides and other compounds capable of interacting with the $C_H2$-$C_H3$ cleft of an immunoglobulin molecule, such that interaction of the immunoglobulin with other molecules (e.g., effectors or other immunoglobulins) is blocked. Methods for identifying such polypeptides and other compounds also are provided, along with compositions and articles of manufacture containing the polypeptides and compounds. These are described in the following subsections.

Immunoglobulins

The immunoglobulins make up a class of proteins found in plasma and other bodily fluids that exhibit antibody activity and bind to other molecules (e.g., antigens and certain cell surface receptors) with a high degree of specificity. Based on their structure and biological activity, immunoglobulins can be divided into five classes: IgM, IgG, IgA, IgD, and IgE. IgG is the most abundant antibody class in the body; this molecule assumes a twisted "Y" shape configuration. With the exception of the IgMs, immunoglobulins are composed mainly of four peptide chains that are linked by several intrachain and interchain disulfide bonds. For example, the IgGs are composed of two polypeptide heavy chains (H chains) and two polypeptide light chains (L chains), which are coupled by disulfide bonds and non-covalent bonds to form a protein molecule with a molecular weight of approximately 160,000 daltons. The average IgG molecule contains approximately 4.5 interchain disulfide bonds and approximately 12 intrachain disulfide bonds (Frangione and Milstein (1968) *J. Mol. Biol.* 33:893-906).

The light and heavy chains of immunoglobulin molecules are composed of constant regions and variable regions (see, e.g., Padlan (1994) *Mol. Immunol.* 31:169-217). For example, the light chains of an IgG1 molecule each contain a variable domain ($V_L$) and a constant domain ($C_L$). The heavy chains each have four domains: an amino terminal variable domain ($V_H$), followed by three constant domains ($C_H1$, $C_H2$, and the carboxy terminal $C_H3$). A hinge region corresponds to a flexible junction between the $C_H1$ and $C_H2$ domains. Papain digestion of an intact IgG molecule results in proteolytic cleavage at the hinge and produces an Fc fragment that contains the $C_H2$ and $C_H3$ domains, and two identical Fab fragments that each contain a $C_H1$, $C_L$, $V_H$, and $V_L$ domain. The Fc fragment has complement- and tissue-binding activity, while the Fab fragments have antigen-binding activity.

Immunoglobulin molecules can interact with other polypeptides through various regions. The majority of antigen binding, for example, occurs through the $V_L/V_H$ region of the Fab fragment. The hinge region also is thought to be important, as immunological dogma states that the binding sites for Fc receptors (FcR) are found in the hinge region of IgG molecules (see, e.g., Raghavan and Bjorkman (1996) *Annu. Rev. Dev. Biol.* 12:181-200). More recent evidence, however, suggests that FcR interacts with the hinge region primarily when the immunoglobulin is monomeric (i.e., not immune-complexed). Such interactions typically involve the amino acids at positions 234-237 of the Ig molecule (Wiens et al. (2000) *J. Immunol.* 164:5313-5318).

Immunoglobulin molecules also can interact with other polypeptides through a cleft within the $C_H2$-$C_H3$ domain. The "$C_H2$-$C_H3$ cleft" typically includes the amino acids at positions 251-255 within the $C_H2$ domain and the amino acids at positions 424-436 within the $C_H3$ domain. As used herein, numbering is with respect to an intact IgG molecule as in Kabat et al. (*Sequences of Proteins of Immunological Interest*, 5th ed., Public Health Service, U.S. Department of Health and Human Services, Bethesda, Md.). The corresponding amino acids in other immunoglobulin classes can be readily determined by those of ordinary skill in the art.

The $C_H2$-$C_H3$ cleft is unusual in that it is characterized by both a high degree of solvent accessibility and a predominantly hydrophobic character, suggesting that burial of an exposed hydrophobic surface is an important driving force behind binding at this site. A three-dimensional change occurs at the IgG $C_H2$-$C_H3$ cleft upon antigen binding, allowing certain residues (e.g., a histidine at position 435) to become exposed and available for binding. Direct evidence of three-dimensional structural changes that occur upon antigen binding was found in a study using monoclonal antibodies sensitive to conformational changes in the Fc region of human IgG. Five IgG epitopes were altered by antigen binding: two within the hinge region and three within the $C_H2$-$C_H3$ cleft. (Girkontraite et al. (1996) *Cancer Biother. Radiopharm.* 11:87-96). Antigen binding therefore can be important for determining whether an immunoglobulin binds to other molecules through the hinge or the Fc $C_H2$-$C_H3$ region.

The Fc region can bind to a number of effector molecules and other proteins, including the following:

(1) FcRn—The neonatal Fc receptor determines the half life of the antibody molecule in the general circulation (Leach et al., (1996) *J. Immunol.* 157:3317-3322; Gheti and Ward (2000) *Ann. Rev. Immunol.* 18:739-766). Mice genetically lacking FcRn are protected from the deleterious effects of pathogenic autoantibodies due to the shortened half-life of the autoantibodies (Liu et al. (1997) *J. Exp. Med.* 186:777-783). An inhibitor of FcRn binding to immune complexes or to pathogenic autoantibodies would be useful in treating diseases involving pathogenic autoantibodies and/or immune complexes.

(2) FcR—The cellular Fc Receptor provides a link between the humoral immune response and cell-mediated effector systems (Hamano et al. (2000) *J. Immunol.* 164: 6113-6119; Coxon et al. (2001) *Immunity* 14:693-704; Fossati et al. (2001) *Eur. J. Clin. Invest.* 31:821-831). The Fcγ Receptors are specific for IgG molecules, and include FcγRI, FcγRIIa, FcγRIIb, and FcγRIII. These isotypes bind with differing affinities to monomeric and immune-complexed IgG.

(3) RF—Rheumatoid factors are immunoglobulins that bind to other immune-complexed immunoglobulin molecules and can exacerbate arthritis in animal models of rheumatoid arthritis (see, e.g., Ezaki et al. (1996) *Clin. Exp. Immunol.* 104:474-482).

(4) Histones—Histones are very basic, positively charged proteins that bind to DNA and the negatively charged basement membrane in the kidneys. In lupus nephritis, histones bind first to the kidneys and then immune complexes bind to these kidney-bound histones (Gussin et al. (2000) *Clin. Immunol.* 96:150-161).

(5) MBP—Myelin Basic Protein is the primary autoimmune target in multiple sclerosis (M S; Sindic et al. (1980) *Clin. Exp. Immunol.* 41:1-7; Poston (1984) *Lancet* 1:1268-1271).

(6) C1q—The first component of the classical complement pathway is C1, which exists in blood serum as a complex of three proteins, C1q, C1r, and C1s. The classical complement pathway is activated when C1q binds to the Fc regions of antigen-bound IgG or IgM. Although the binding of C1q to a single Fc region is weak, C1q can form tight bonds to a cluster of Fc regions. At this point C1 becomes proteolytically active.

The formation of immune complexes via interactions between immunoglobulin Fc regions and other antibodies or other factors (e.g., those described above) is referred to herein as "Fc-mediated immune complex formation" or "the Fc-mediated formation of an immune complex." Immune complexes containing such interactions are termed "Fc-mediated immune complexes." Fc-mediated immune complexes can include immunoglobulin molecules with or without bound antigen, and typically include $C_H2$-$C_H3$ cleft-specific ligands that have higher binding affinity for immune complexed antibodies than for monomeric antibodies. The large, generally insoluble complexes that can result from Fc-mediated immune complex formation typically are involved in the pathology of diseases such as, for example, RA and lupus nephritis.

Purified Polypeptides

As used herein, a "polypeptide" is any chain of amino acid residues, regardless of post-translational modification (e.g., phosphorylation or glycosylation). Polypeptides of the invention typically are between 11 and 50 amino acids in length (e.g., 11, 12, 13, 14, 15, 20, 25, 30, 35, 40, 45, or 50 amino acids in length). Polypeptides of the invention that are between 10 and 20 amino acids in length (e.g., 10, 11, 12, 13, 14, 15, 16, 17, 18, 19, or 20 amino acids in length) are particularly useful.

The amino acid sequences of the polypeptides of the invention are somewhat constrained, but can have some variability. For example, a polypeptide can have an amino acid sequence consisting of $Xaa_1$-Cys-Ala-$Xaa_2$-His-$Xaa_3$-$Xaa_4$-$Xaa_5$-Leu-Val-Trp-Cys-$Xaa_6$ (SEQ ID NO:1), wherein the groups of amino acids denoted by $Xaa_n$ can display significant variability. For example, $Xaa_1$ can be absent or can be any amino acid. $Xaa_2$ typically can be any non-aromatic amino acid (i.e., any amino acid other than Phe, Tyr, or Trp), other than Ala. $Xaa_3$ can be any amino acid. $Xaa_4$ typically can be Gly or Ala, while Xaas can be Glu or Ala. Like $Xaa_1$, $Xaa_6$ also can be absent or can be any amino acid. A polypeptide having the amino acid sequence Arg-Cys-Ala-Arg-His-Leu-Gly-Glu-Leu-Val-Trp-Cys-Thr (SEQ ID NO:2) is particularly useful, and as described herein, can bind to the $C_H2$-$C_H3$ cleft of an immunoglobulin molecule to inhibit the Fc-mediated formation of insoluble immune complexes.

Alternatively, a polypeptide can contain the amino acid sequence Cys-Ala-$Xaa_1$-His-$Xaa_2$-$Xaa_3$-$Xaa_4$-Leu-Val-Trp-Cys (SEQ ID NO:3), in which $Xaa_1$ can be any non-aromatic amino acid other than Ala (i.e., any amino acid other than Phe, Tyr, Trp, or Ala), $Xaa_2$ can be any amino acid, $Xaa_3$ can be Gly or Ala, and $Xaa_4$ can be Glu or Ala.

Polypeptides of the invention may be modified for use in vivo by the addition, at the amino- or carboxy-terminal end, of a stabilizing agent to facilitate survival of the polypeptide in vivo. This can be useful in situations in which peptide termini tend to be degraded by proteases prior to cellular uptake. Such blocking agents can include, without limitation, additional related or unrelated peptide sequences that can be attached to the amino- and/or carboxy-terminal residues of the polypeptide (e.g., an acetyl group attached to the N-terminal amino acid or an amide group attached to the C-terminal amino acid). Such attachment can be achieved either chemically, during the synthesis of the polypeptide, or by recombinant DNA technology using methods familiar to those of ordinary skill in the art. Alternatively, blocking agents such as pyroglutamic acid or other molecules known in the art can be attached to the amino- and/or carboxy-terminal residues, or the amino group at the amino terminus or the carboxy group at the carboxy terminus can be replaced with a different moiety. A proline or an Ala-Pro-Pro sequence at the amino terminus can be particularly useful (see, e.g., WO 00/22112).

Polypeptides also can contain an amino acid tag. A "tag" is generally a short amino acid sequence that provides a ready means of detection or purification through interactions with an antibody against the tag or through other compounds or molecules that recognize the tag. For example, tags such as c-myc, hemagglutinin, polyhistidine, or Flag® can be used to aid purification and detection of a polypeptide. As an example, a polypeptide with a polyhistidine tag can be purified based on the affinity of histidine residues for nickel ions (e.g., on a Ni-NTA column), and can be detected in western blots by an antibody against polyhistidine (e.g., the Penta-His antibody; Qiagen, Valencia, Calif.). Tags can be inserted anywhere within the polypeptide sequence, although, insertion at the amino- or carboxy-terminus is particularly useful.

The term "amino acid" refers to natural amino acids, unnatural amino acids, and amino acid analogs, all in their D and L stereoisomers if their structures so allow. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine, and pipecolic acid.

An "analog" is a chemical compound that is structurally similar to another but differs slightly in composition (as in the replacement of one atom by an atom of a different element or in the presence of a particular functional group). An "amino acid analog" therefore is structurally similar to a naturally occurring amino acid molecule as is typically found in native polypeptides, but differs in composition such that either the C-terminal carboxy group, the N-terminal amino group, or the side-chain functional group has been chemically modified to another functional group. Amino acid analogs include natural and unnatural amino acids which are chemically blocked, reversibly or irreversibly, or modified on their N-terminal amino group or their side-chain groups, and include, for example, methionine sulfoxide, methionine sulfone, S-(carboxymethyl)-cysteine, S-(carboxymethyl)-cysteine sulfoxide and S-(carboxymethyl)-cysteine sulfone. Amino acid analogs may be naturally occurring, or can be synthetically prepared. Non-limiting examples of amino acid analogs include aspartic acid-(beta-methyl ester), an analog of aspartic acid; N-ethylglycine, an analog of glycine; and alanine carboxamide, an analog of alanine. Other examples of amino acids and amino acids analogs are listed in Gross and Meienhofer, *The Peptides: Analysis, Synthesis, Biology*, Academic Press, Inc., New York (1983).

The stereochemistry of a polypeptide can be described in terms of the topochemical arrangement of the side chains of the amino acid residues-about the polypeptide backbone, which is defined by the peptide bonds between the amino acid residues and the α-carbon atoms of the bonded residues. In addition, polypeptide backbones have distinct termini and thus direction. The majority of naturally occurring amino acids are L-amino acids. Naturally occurring polypeptides are largely comprised of L-amino acids.

D-amino acids are the enantiomers of L-amino acids and can form peptides that are herein referred to as "inverso" polypeptides (i.e., peptides corresponding to native peptides but made up of D-amino acids rather than L-amino acids). A "retro" polypeptide is made up of L-amino acids, but has an amino acid sequence in which the amino acid residues are assembled in the opposite direction of the native peptide sequence.

"Retro-inverso" modification of naturally occurring polypeptides involves the synthetic assembly of amino acids with a carbon stereochemistry opposite to that of the corresponding L-amino acids (i.e., D- or D-allo-amino acids), in reverse order with respect to the native polypeptide sequence. A retro-inverso analog thus has reversed termini and reversed direction of peptide bonds, while approximately maintaining the topology of the side chains as in the native peptide sequence. The term "native" refers to any sequence of L-amino acids used as a starting sequence for the preparation of partial or complete retro, inverso or retro-inverso analogs.

Partial retro-inverso polypeptide analogs are polypeptides in which only part of the sequence is reversed and replaced with enantiomeric amino acid residues. Since the retro-inverted portion of such an analog has reversed amino and carboxyl termini, the amino acid residues flanking the retro-inverted portion can be replaced by side-chain-analogous α-substituted geminal-diaminomethanes and malonates, respectively. Alternatively, a polypeptide can be a complete retro-inverso analog, in which the entire sequence is reversed and replaced with D-amino acids.

The invention also provides peptidomimetic compounds that are designed on the basis of the amino acid sequences of polypeptides. Peptidomimetic compounds are synthetic, non-peptide compounds having a three-dimensional conformation (i.e., a "peptide motif,") that is substantially the same as the three-dimensional conformation of a selected peptide, and can thus confer the same or similar function as the selected peptide. Peptidomimetic compounds of the invention can be designed to mimic any of the polypeptides of the invention.

Peptidomimetic compounds that are protease resistant are particularly useful. Furthermore, peptidomimetic compounds m ay have additional characteristics that enhance therapeutic utility, such as increased cell permeability and prolonged biological half-life. Such compounds typically have a backbone that is partially or completely non-peptide, but with side groups that are identical or similar to the side groups of the amino acid residues that occur in the peptide upon which the peptidomimetic compound is based. Several types of chemical bonds (e.g., ester, thioester, thioamide, retroamide, reduced carbonyl, dimethylene and ketomethylene) are known in the art to be useful substitutes for peptide bonds in the construction of peptidomimetic compounds.

The interactions between a polypeptide of the invention and an immunoglobulin molecule typically occur through the $C_H2$-$C_H3$ cleft of the immunoglobulin. Such interactions are engendered through physical proximity and are mediated by, for example, hydrophobic interactions. The "binding affinity" of a polypeptide for an immunoglobulin molecule refers to the strength of the interaction between the polypeptide and the immunoglobulin. Binding affinity typically is expressed as an equilibrium dissociation constant ($K_d$), which is calculated as $K_d = k_{off}/k_{on}$, where $k_{off}$=the kinetic dissociation constant of the reaction, and $k_{on}$=the kinetic association constant of the reaction. $K_d$ is expressed as a concentration, with a low $K_d$ value (e.g., less than 100 nM) signifying high affinity. Polypeptides of the invention that can interact with an immunoglobulin molecule typically have a binding affinity of at least 1 μM (e.g., at least 500 nM, at least 100 nM, at least 50 nM, or at least 10 nM) for the $C_H2$-$C_H3$ cleft of the immunoglobulin.

Polypeptides of the invention typically have a higher binding affinity (e.g., at least 10-fold, at least 100-fold, or at least 1000-fold higher binding affinity), for immunoglobulin molecules that are bound by antigen than for monomeric immunoglobulins. Conformational changes that occur within the Fc region of an immunoglobulin molecule upon antigen binding to the Fab region are likely involved in this difference in affinity. The crystal structures of bound and unbound NC6.8 Fab (from a murine monoclonal antibody) showed that the tail of the Fab heavy chain was displaced by 19 angstroms in crystals of the antigen/antibody complex, as compared to its position in unbound Fab (Guddat et al. (1994) *J. Mol. Biol.* 236-247-274). Since the C-terminal tail of the Fab region is connected to the Fc region in an intact antibody, this shift would be expected to affect the conformation of the $C_H2$-$C_H3$ cleft. Furthermore, examination of several three-dimensional structures of intact immunoglobulins revealed a direct physical connection between the Fab heavy chain and the Fc $C_H2$-$C_H3$ cleft (Harris et al. (1997) *Biochemistry* 36:1581-1597; Saphire et al. (2001) *Science* 293:1155-1159).

Molecular modeling of the $C_H2$-$C_H3$ cleft of monomeric (i.e., unbound) and immune-complexed IgG (see FIGS. 1A and 1B) revealed that the monomeric Fc $C_H2$-$C_H3$ cleft has a closed configuration, which can prevent binding to critical amino acid residues (e.g., His435; see, for example, O'Brien et al. (1994) *Arch. Biochem. Biophys.* 310:25-31; Jefferies et al. (1984) *Immunol. Lett.* 7:191-194; and West et al. (2000) *Biochemistry* 39:9698-9708). Immune-complexed (antigen-bound) IgG, however, has a more open configuration and thus is more conducive to ligand binding. The binding affinity of RF for immune-complexed IgG, for example, is much greater than the binding affinity of RF for monomeric IgG (Corper et al. (1997) *Nat. Struct. Biol.* 4:374; Sohi et al. (1996) *Immunol.* 88:636). The same typically is true for polypeptides of the invention.

Because polypeptides of the invention can bind to the $C_H2$-$C_H3$ cleft of immunoglobulin molecules, they are useful for blocking the interaction of other factors (e.g., FcRn, FcR, RF, histones, MBP, and other immunoglobulins) to the Fc region of the immunoglobulin, and thus can inhibit Fc-mediated immune complex formation. By "inhibit" is meant that Fc-mediated immune complex formation is reduced in the presence of a polypeptide of the invention, as compared to the level of immune complex formation in the absence of the polypeptide. Such inhibiting can occur in vitro (e.g., in a test tube) or in vivo (e.g., in an individual). Any suitable method can be used to assess the level of immune complex formation. Many such methods are known in the art, and some of these are described herein.

Polypeptides of the invention typically interact with the $C_H2$-$C_H3$ cleft of an immunoglobulin molecule in a monomeric fashion (i.e., interact with only one immunoglobulin molecule and thus do not link two or more immunoglobulin molecules together). Interactions with other immunoglobulin molecules through the Fc region therefore are precluded by the presence of the polypeptide. The inhibition of Fc-mediated immune complex formation can be assessed in vitro, for example, by incubating an IgG molecule with a labeled immunoglobulin molecule (e.g., a fluorescently labeled RF molecule) in the presence and absence of a polypeptide of the invention, and measuring the amount of labeled immunoglobulin that is incorporated into an immune complex. Other methods suitable for detecting immune complex formation also may be used, as discussed below.

Preparation and Purification of Polypeptides

Polypeptides of the invention can be produced by a number of methods, many of which are well known in the art. By way of example and not limitation, a polypeptide can be obtained by extraction from a natural source (e.g., from isolated cells, tissues or bodily fluids), by expression of a recombinant nucleic acid encoding the polypeptide (as, for example, described below), or by chemical synthesis (e.g., by solid-phase synthesis or other methods well known in the art, including synthesis with an ABI peptide synthesizer; Applied Biosystems, Foster City, Calif.). Methods for synthesizing retro-inverso polypeptide analogs (Bonelli et al. (1984) *Int. J. Peptide Protein Res.* 24:553-556; and Verdini and Viscomi (1985) *J. Chem. Soc. Perkin Trans. I*:697-701), and some processes for the solid-phase synthesis of partial retro-inverso peptide analogs also have been described (see, for example, European Patent number EP0097994).

The invention provides isolated nucleic acid molecules encoding the polypeptides described herein. As used herein, "nucleic acid" refers to both RNA and DNA, including cDNA, genomic DNA, and synthetic (e.g., chemically synthesized) DNA. The nucleic acid can be double-stranded or single-stranded (i.e., a sense or an antisense single strand). The term "isolated" as used herein with reference to a nucleic acid refers to a naturally-occurring nucleic acid that is not immediately contiguous with both of the sequences with which it is immediately contiguous (one at the 5' end and one at the 3' end) in the naturally-occurring genome of the organism from which it is derived. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences that is normally immediately contiguous with the DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

The invention also provides vectors containing the nucleic acids described herein. As used herein, a "vector" is a replicon, such as a plasmid, phage, or cosmid, into which another DNA segment may be inserted so as to bring about the replication of the inserted segment. The vectors of the invention are preferably expression vectors, in which the nucleotides encode the polypeptides of the invention with an initiator methionine, operably linked to expression control sequences. As used herein, "operably linked" means incorporated into a genetic construct so that expression control sequences effectively control expression of a coding sequence of interest. An "expression control sequence" is a DNA sequence that controls and regulates the transcription and translation of another DNA sequence, and an "expression vector" is a vector that includes expression control sequences, so that a relevant DNA segment incorporated into the vector is transcribed and translated. A coding sequence is "operably linked" and "under the control" of transcriptional and translational control sequences in a cell when RNA polymerase transcribes the coding sequence into mRNA, which then is translated into the protein encoded by the coding sequence.

Methods well known to those skilled in the art may be used to subclone isolated nucleic acid molecules encoding polypeptides of interest into expression vectors containing relevant coding sequences and appropriate transcriptional/translational control signals. See, for example, Sambrook et al., *Molecular Cloning: A Laboratory Manual* ($2^{nd}$ edition), Cold. Spring Harbor Laboratory, New York (1989); and Ausuble et al., *Current Protocols in Molecular Biology*, Green Publishing Associates and Wiley Interscience, New York (1989). Expression vectors of the invention can be used in a variety of systems (e.g., bacteria, yeast, insect cells, and mammalian cells), as described herein. Examples of suitable expression vectors include, without limitation, plasmids and viral vectors derived from, for example, herpes viruses, retroviruses, vaccinia viruses, adenoviruses, and adeno-associated viruses. A wide variety of suitable expression vectors and systems are commercially available, including the pET series of bacterial expression vectors (Novagen, Madison, Wis.), the Adeno-X expression system (Clontech), the Baculogold baculovirus expression system (BD Biosciences Pharmingen, San Diego, Calif.), and the pCMV-Tag vectors (Stratagene, La Jolla, Calif.).

Expression vectors that encode the polypeptides of the invention can be used to produce the polypeptides. Expression systems that can be used for small or large scale production of the polypeptide of the invention include, but are not limited to, microorganisms such as bacteria (e.g., *E. coli* and *B. subtilis*) transformed with recombinant bacteriophage DNA, plasmid DNA, or cosmid DNA expression vectors containing the nucleic acid molecules of the invention; yeast (e.g., *S. cerevisiae*) transformed with recombinant yeast expression vectors containing the nucleic acid molecules of the invention; insect cell systems infected with recombinant virus expression vectors (e.g., baculovirus) containing the nucleic acid molecules of the invention; plant cell systems infected with recombinant virus expression vectors (e.g., tobacco mosaic virus) or transformed with recombinant plasmid expression vectors (e.g., Ti plasmid) containing the nucleic acid molecules of the invention; or mammalian cell systems (e.g., primary cells or immortalized cell lines such as COS cells, CHO cells, HeLa cells, HEK 293 cells, and 3T3 L1 cells) harboring recombinant expression constructs containing promoters derived from the genome of mammalian cells (e.g., the metallothionein promoter) or from mammalian viruses (e.g., the adenovirus late promoter and the cytomegalovirus promoter), along with the nucleic acids of the invention.

The term "purified polypeptide" as used herein refers to a polypeptide that either has no naturally occurring counterpart (e.g., a peptidomimetic), or has been chemically synthesized and is thus uncontaminated by other polypeptides, or that has been separated or purified from other cellular components by which it is naturally accompanied (e.g., other cellular proteins, polynucleotides, or cellular components). Typically, the polypeptide is considered "purified" when it is at least 70%, by dry weight, free from the proteins and. naturally occurring organic molecules with which it naturally associates. A preparation of the purified polypeptide of the invention therefore can be, for example, at least 80%, at least 90%, or at least 99%, by dry weight, the polypeptide of the invention. Suitable methods for purifyng the polypeptides of the invention can include, for example, affinity chromatography, immunoprecipitation, size exclusion chromatography, and ion exchange chromatography. The extent of purification can be measured by any appropriate method, including but not limited to: column chromatography, polyacrylamide gel electrophoresis, or high-performance liquid chromatography.

Methods of Modeling, Designing, and Identifying Compounds

The invention provides methods for designing, modeling, and identifying compounds that can bind to the $C_H2$-$C_H3$ cleft of an immunoglobulin molecule and thus serve as inhibitors of Fc-mediated immune complex formation. Such compounds also are referred to herein as "ligands." Compounds designed, modeled, and identified by methods of the invention typically can interact with an immunoglobulin molecule through the $C_H2$-$C_H3$ cleft, and typically have a binding affinity of at least 1 μM (e.g., at least 500 nM, at least 100 nM, at least 50 nM, or at least 10 nM) for the $C_H2$-$C_H3$ cleft of the immunoglobulin. Such compounds generally have higher binding affinity (e.g., at least 10-fold, at least 100-fold, or at least 1000-fold higher binding affinity) for immune-complexed immunoglobulin molecules than for monomeric immunoglobulin molecules.

Compounds of the invention typically interact with the $C_H2$-$C_H3$ cleft of an immunoglobulin molecule in a monomeric fashion (i.e., interact with only one immunoglobulin molecule and thus do not link two or more immunoglobulin molecules together). The interactions between a compound and an immunoglobulin molecule typically involve the amino acid residues at positions 252, 253, 435, and 436 of the immunoglobulin (number according to Kabat, supra). The interaction between compounds of the invention and the $C_H2$-$C_H3$ cleft renders the compounds capable of inhibiting the Fc-mediated formation of immune complexes by blocking the binding of other factors (e.g., RF, histones, FcR, FcRn, C1q, MBP, and psoriasis associated antigen pso p27) to the $C_H2$-$C_H3$ cleft.

Compounds identified by methods of the invention can be polypeptides such as, for example, those described herein. Alternatively, a compound can be any suitable type of molecule that can specifically bind to the $C_H2$-$C_H3$ cleft of an immunoglobulin molecule. Compounds such as quercitin, boswellic acids, and statins are particularly useful.

By "modeling" is meant quantitative and/or qualitative analysis of receptor-ligand structure/function based on three-dimensional structural information and receptor-ligand interaction models. This includes conventional numeric-based molecular dynamic and energy minimization models, interactive computer graphic models, modified molecular mechanics models, distance geometry and other structure-based constraint models. Modeling typically is performed using a computer and may be further optimized using known methods.

Methods of designing ligands that bind specifically (i.e., with high affinity) to the $C_H2$-$C_H3$ cleft of an immunoglobulin molecule having bound antigen typically are computer-based, and involve the use of a computer having a program capable of generating an atomic model. Computer programs that use X-ray crystallography data are particularly useful for designing ligands that can interact with an Fc $C_H2$-$C_H3$ cleft. Programs such as RasMol, for example, can be used to generate a three dimensional model of a $C_H2$-$C_H3$ cleft and/or determine the structures involved in ligand binding. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures.

Methods of the invention can include, for example, providing to a computer the atomic structural coordinates (e.g., the coordinates shown in FIGS. 2A and 2B) for amino acid residues within the $C_H2$-$C_H3$ cleft (e.g., amino acid residues at positions 252, 253, 435, and 436 of the cleft) of an immunoglobulin molecule in an Fc-mediated immune complex, using the computer to generate an atomic model of the $C_H2$-$C_H3$ cleft, further providing the atomic structural coordinates of a candidate compound and generating an atomic model of the compound optimally positioned within the $C_H2$-$C_H3$ cleft, and identifying the candidate compound as a ligand of interest if the compound interacts with the amino acid residues at positions 252, 253, 435, and 436 of the cleft. The data provided to the computer also can include the atomic coordinates of amino acid residues at positions in addition to 252, 253, 435, and 436. By "optimally positioned" is meant positioned to optimize hydrophobic interactions between the candidate compound and the amino acid residues at positions 252, 253, 435, and 436 of the $C_H2$-$C_H3$ cleft.

Alternatively, a method for designing a ligand having specific binding affinity for the $C_H2$-$C_H3$ cleft of an immunoglobulin molecule can utilize a computer with an atomic model of the cleft stored in its memory. The atomic coordinates of a candidate compound then can be provided to the computer, and an atomic model of the candidate compound optimally positioned can be generated. As described herein, a candidate compound can be identified as a ligand having specific binding affinity for the $C_H2$-$C_H3$ cleft of an immunoglobulin molecule if, for example, the compound interacts with the amino acid residues at positions 252, 253, 435, and 436 of the cleft.

Compounds of the invention also may be interactively designed from structural information of the compounds described herein using other structure-based design/modeling techniques (see, e.g., Jackson (1997) Seminars in Oncology 24:L164-172; and Jones et al. (1996) J. Med. Chem. 39:904-917).

Compounds and polypeptides of the invention also can be identified by, for example, identifying candidate compounds by computer modeling as fitting spatially and preferentially (i.e., with high affinity) into the $C_H2$-$C_H3$ cleft of an immunoglobulin molecule, and then screening those compounds in vitro or in vivo for the ability to inhibit Fc-mediated immune complex formation. Suitable methods for such in vitro and in vivo screening include those described herein.

Compositions and Articles of Manufacture

The invention provides methods for treating conditions that arise from abnormal Fc-mediated immune complex formation (e.g., over-production of Fc-mediated immune complexes). By these methods, polypeptides and compounds in accordance with the invention are administered to a subject (e.g., a human or another mammal) having a disease or disorder (e.g., rheumatoid arthritis) that can be alleviated by modulating Fc-mediated immune complex formation. Typically, one or more polypeptides or compounds can be administered to a subject suspected of having a disease or condition associated with immune complex formation.

Compositions of the invention typically contain one or more polypeptides and compounds described herein. A $C_H2$-$C_H3$ binding polypeptide, for example, can be in a pharmaceutically acceptable carrier or diluent, and can be administered in amounts and for periods of time that will vary depending upon the nature of the particular disease, its severity, and the subject's overall condition. Typically, the polypeptide is administered in an inhibitory amount (i.e., in an amount that is effective for inhibiting the production of immune complexes in the cells or tissues contacted by the polypeptide). The polypeptide and methods of the invention also can be used prophylactically, e.g., to minimize, immunoreactivity in a subject at risk for abnormal or over-production of immune complexes (e.g., a transplant recipient).

The ability of a polypeptide to inhibit Fc-mediated immune complex formation can be assessed by, for example, measuring immune complex levels in a subject before and after treatment. A number of methods can be used to measure immune complex levels in tissues or biological samples, including those that are well known in the art. If the subject is a research animal, for example, immune complex levels in the joints can be assessed by immunostaining following euthanasia. The effectiveness of an inhibitory polypeptide also can be assessed by direct methods such as measuring the level of circulating immune complexes in serum samples. Alternatively, indirect methods can be used to evaluate the effectiveness of polypeptides in live subjects. For example, reduced immune complex formation can be inferred from reduced pain in rheumatoid arthritis patients. Animal models also can be used to study the development of and relief from conditions such as rheumatoid arthritis.

Methods for formulating and subsequently administering therapeutic compositions are well known to those skilled in the art. Dosing is generally dependent on, the severity and responsiveness of the disease state to be treated, with the course of treatment lasting from several days to several months, or until a cure is effected or a diminution of the disease state is achieved. Persons of ordinary skill in the art routinely determine optimum dosages, dosing methodologies and repetition rates. Optimum dosages can vary depending on the relative potency of individual polypeptides, and can generally be estimated based on EC50 found to be effective in in vitro and in vivo animal models. Typically, dosage is from 0.01 μg to 100 g per kg of body weight, and may be given once or more daily, biweekly, weekly, monthly, or even less often. Following successful treatment, it may be desirable to have the patient undergo maintenance therapy to prevent the recurrence of the disease state.

The present invention provides pharmaceutical compositions and formulations that include the polypeptides and/or compounds of the invention. Polypeptides therefore can be admixed, encapsulated, conjugated or otherwise associated with other molecules, molecular structures, or mixtures of compounds such as, for example, liposomes, polyethylene glycol, receptor targeted molecules, or oral, rectal, topical or other formulations, for assisting in uptake, distribution and/or absorption.

A "pharmaceutically acceptable carrier" (also referred to herein as an "excipient") is a pharmaceutically acceptable solvent, suspending agent, or any other pharmacologically inert vehicle for delivering one or more therapeutic compounds (e.g., $C_H2$-$C_H3$ binding polypeptides) to a subject. Pharmaceutically acceptable carriers can be liquid or solid, and can be selected with the planned manner of administration in mind so as to provide for the desired bulk, consistency, and other pertinent transport and chemical properties, when combined with one or more of therapeutic compounds and any other components of a given pharmaceutical composition. Typical pharmaceutically acceptable carriers that do not deleteriously react with amino acids include, by way of example and not limitation: water; saline solution; binding agents (e.g., polyvinylpyrrolidone or hydroxypropyl methylcellulose); fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

The pharmaceutical compositions of the present invention can be administered by a number of methods, depending upon whether local or systemic treatment is desired and upon the area to be treated. Administration can be, for example, topical (e.g., transdermal, sublingual, ophthalmic, or intranasal); pulmonary (e.g., by inhalation or insufflation of powders or aerosols); oral; or parenteral (e.g., by subcutaneous, intrathecal, intraventricular, intramuscular, or intraperitoneal injection, or by intravenous drip). Administration can be rapid (e.g., by injection) or can occur over a period of time (e.g., by slow. infusion or administration of slow release formulations). For treating tissues in the central nervous system, $C_H2$-$C_H3$ binding polypeptides can be administered by injection or infusion into the cerebrospinal fluid, preferably with one or more agents capable of promoting penetration of the polypeptides across the blood-brain barrier.

Formulations for topical administration of $C_H2$-$C_H3$ binding polypeptides include, for example, sterile and non-sterile aqueous solutions, non-aqueous solutions in common solvents such as alcohols, or solutions in liquid or solid oil bases. Such solutions also can contain buffers, diluents and other suitable additives. Pharmaceutical compositions and formulations for topical administration can include transdermal patches, ointments, lotions, creams, gels, drops, suppositories, sprays, liquids, and powders. Nasal sprays are particularly useful, and can be administered by, for example, a nebulizer or another nasal spray device. Administration by an inhaler also is particularly useful. Conventional pharmaceutical carriers, aqueous, powder or oily bases, thickeners and the like may be necessary or desirable.

Compositions and formulations for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders.

Compositions and formulations for parenteral, intrathecal or intraventricular administration can include sterile aqueous solutions, which also can contain buffers, diluents and other suitable additives (e.g., penetration enhancers, carrier compounds and other pharmaceutically acceptable carriers).

Pharmaceutical compositions of the present invention include, but are not limited to, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations have been widely used for oral delivery of therapeutics due to their ease of formulation and efficacy of solubilization, absorption, and bioavailability.

Liposomes are vesicles that have a membrane formed from a lipophilic material and an aqueous interior that can contain the composition to be delivered. Liposomes can be particularly useful due to their specificity and the duration of action they offer from the standpoint of drug delivery. Liposome compositions can be formed, for example, from phosphatidylcholine, dimyristoyl phosphatidylcholine, dipalmitoyl phosphatidylcholine, dimyristoyl phosphatidylglycerol, or dioleoyl phosphatidylethanolamine. Numerous lipophilic agents are commercially available, including Lipofectin®

(Invitrogen/Life Technologies, Carlsbad, Calif.) and Effectenem™ (Qiagen, Valencia, Calif.).

Polypeptides of the invention further encompass any pharmaceutically acceptable salts, esters, or salts of such esters, or any other compound which, upon administration to an animal including a human, is capable of providing (directly or indirectly) the biologically active metabolite or residue thereof. Accordingly, for example, the invention provides pharmaceutically acceptable salts of polypeptides, prodrugs and pharmaceutically acceptable salts of such prodrugs, and other bioequivalents. The term "prodrug" indicates a therapeutic agent that is prepared in an inactive form and is converted to an active form (i.e., drug) within the body or cells thereof by the action of endogenous enzymes or other chemicals and/or conditions. The term "pharmaceutically acceptable salts" refers to physiologically and pharmaceutically acceptable salts of the polypeptides of the invention (i.e., salts that retain the desired biological activity of the parent polypeptide without imparting undesired toxicological effects). Examples of pharmaceutically acceptable salts include, but are not limited to, salts formed with cations (e.g., sodium, potassium, calcium, or polyamines such as spermine); acid addition salts formed with inorganic acids (e.g., hydrochloric acid, hydrobromic acid, sulfuric acid, phosphoric acid, or nitric acid); and salts formed with organic acids (e.g., acetic acid, citric acid, oxalic acid, palmitic acid, or fumaric acid).

Pharmaceutical compositions containing the polypeptides of the present invention also can incorporate penetration enhancers that promote the efficient delivery of polypeptides to the skin of animals. Penetration enhancers can enhance the diffusion of both lipophilic and non-lipophilic drugs across cell membranes. Penetration enhancers can be classified as belonging to one of five broad categories, i.e., surfactants (e.g., sodium lauryl sulfate, polyoxyethylene-9-lauryl ether and polyoxyethylene-20-cetyl ether); fatty acids (e.g., oleic acid, lauric acid, myristic acid, palmitic acid, and stearic acid); bile salts (e.g., cholic acid, dehydrocholic acid, and deoxycholic acid); chelating agents (e.g., disodium ethylenediaminetetraacetate, citric acid, and salicylates); and non-chelating non-surfactants (e.g., unsaturated cyclic ureas). Alternatively, inhibitory polypeptides can be delivered via iontophoresis, which involves a transdermal patch with an electrical charge to "drive" the polypeptide through the dermis.

Certain embodiments of the invention provide pharmaceutical compositions containing (a) one or more polypeptides and (b) one or more other agents that function by a different mechanism. For example, anti-inflammatory drugs, including but not limited to nonsteroidal anti-inflammatory drugs and corticosteroids, and antiviral drugs, including but not limited to ribivirin, vidarabine, acyclovir and ganciclovir, can be included in compositions of the invention. Other non-polypeptide agents (e.g., chemotherapeutic agents) also are within the scope of this invention. Such combined compounds can be used together or sequentially.

Compositions of the present invention additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions of the present invention, such as dyes, flavoring agents, preservatives, antioxidants, opacifiers, thickening agents and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, and aromatic substances. When added, however, such materials should not unduly interfere with the biological activities of the polypeptide components within the compositions of the present invention. The formulations can be sterilized if desired.

The pharmaceutical formulations of the present invention, which can be presented conveniently in unit dosage form, can be prepared according to conventional techniques well known in the pharmaceutical industry. Such techniques include the step of bringing into association the active ingredients (e.g., the $C_H2$-$C_H3$ binding polypeptides of the invention) with the desired pharmaceutical carrier(s) or excipient(s). Typically, the formulations can be prepared by uniformly and bringing the active ingredients into intimate association with liquid carriers or finely divided solid carriers or both, and then, if necessary, shaping the is product. Formulations can be sterilized if desired, provided that the method of sterilization does not interfere with the effectiveness of the polypeptide contained in the formulation.

The compositions of the present invention can be formulated into any of many possible dosage forms such as, but not limited to, tablets, capsules, liquid syrups, soft gels, suppositories, and enemas. The compositions of the present invention also can be formulated as suspensions in aqueous, non-aqueous or mixed media. Aqueous suspensions further can contain substances that increase the viscosity of the suspension including, for example, sodium carboxymethylcellulose, sorbitol, and/or dextran. Suspensions also can contain stabilizers.

$C_H2$-$C_H3$ binding polypeptides of the invention can be combined with packaging material and sold as kits for reducing Fc-mediated immune complex formation. Components and methods for producing articles of manufacture are well known. The articles of manufacture may combine one or more of the polypeptides and compounds set out in the above sections. In addition, the article of manufacture further may include, for example, buffers or other control reagents for reducing or monitoring reduced immune complex formation. Instructions describing how the polypeptides are effective for reducing Fc-mediated immune complex formation can be included in such kits.

Methods for Using $C_H2$-$C_H3$ Binding Compounds and Polypeptides to Inhibit Fc-mediated Immune Complex Formation $C_H2$-$C_H3$ binding polypeptides can be used in in vitro assays of Fc-mediated immune complex formation. Such methods are useful to, for example, evaluate the ability of a $C_H2$-$C_H3$ cleft binding polypeptide to block Fc-mediated immune complex formation. In vitro methods can involve, for example, contacting an immunoglobulin molecule (e.g., an antigen bound immunoglobulin molecule) with an effector molecule (e.g., RF, FcR, FcRn, a histone, MBP, or another antibody) in the presence and absence of a polypeptide of the invention, and determining the level of immune complex formation in each sample. Levels of immune complex formation can be evaluated by, for example, polyacrylamide gel electrophoresis with Coomassie blue or silver staining, or by co-immunoptecipitation. Such methods are known to those of ordinary skill in the art.

Methods of the invention also can be used to treat autoimmune diseases by inhibiting Fc-mediated immune complex formation in an individual. Such methods can involve, for example, administering the $C_H2$-$C_H3$ binding polypeptide of the invention (e.g., contained within a composition of the invention) to a subject having, for example, rheumatoid arthritis (RA), systemic lupus erythematosus (SLE), lupus nephritis, autoimmune glomerulonephritis, atherosclerosis, multiple sclerosis (MS), Parkinson's disease, Crohn's disease, psoriasis, ankylosing spondylitis (AS), or cancer, or to a transplant recipient. These conditions and the involvement of Fc-mediated immune complex formation are described in the subsections below. Methods of the invention also can include steps for identifying a subject in need of such treatment and/or monitoring treated individuals for a reduction in symptoms or levels of immune complex formation.

Rheumatoid Arthritis—RA is characterized by chronic joint inflammation that eventually leads to irreversible cartilage destruction. In RA, abnormal IgG antibodies are produced by lymphocytes in the synovial membranes. These abnormal IgG antibodies then act as antigens. Other IgG and IgM antibodies, termed Rheumatoid Factors (RF), are present in sera and synovia and subsequently react with these abnormal IgG antibody/antigens to produce immune complexes. Immune complexes containing RF are abundant in synovial tissue of patients with RA. RF are directed to the Fc region of IgG, and interact with the $C_H2$-$C_H3$ cleft (Zack et al. (1995) *J. Immunol.* 155:5057-5063). The presence of RF is associated with systemic symptoms, joint erosion, and poor prognosis, although the exact role of RF in RA remains to be fully elucidated.

Collagen II (CII) induced arthritis, a murine model of RA, is characterized by polyarthritis, synovial hyperplasia, infiltration of mononuclear cells, pannus formation and the destruction of cartilage and bone. Mice that are deficient for FcγRI and FcγRIII are protected from CII induced arthritis, suggesting that blockade of FcγRs is useful for treating RA (Kleinau et al. (2000) *J. Exp. Med.* 191:1611-1616). While the etiology of RA is not fully understood, individuals that are genetically predisposed to developing the disease produce high levels of anti-CII antibodies. Immunization with immune complexes containing CII produces anti-idiotypic anti-CII antibodies that have been shown to actually be RF (Holmdahl et al. (1986) *Scand. J. Immunol.* 24; 197-203). Inhibitors that bind to the IgG $C_H2$-$C_H3$ cleft will block this cyclic production of anti-CII and RF anti-idiotypic antibodies.

The inflammation and subsequent cartilage damage caused by immune complexes in RA may be related to the occurrence of FcγRs on macrophages (Blom et al. (2000) *Arthritis Res.* 2:489-503). The absence of functional FcγRI and FcγRIII in knock-out mice prevented inflammation and cartilage destruction after induction of immune complex-mediated arthritis, whereas high basal expression of FcγRs on resident joint macrophages of similarly treated mice susceptible to autoimmune arthritis was correlated with markedly more synovial inflammation and cartilage destruction. In recent studies, the importance of these receptors in inflammation and tissue damage has been shown in various inflammatory diseases, including autoimmune hemolytic anemia and thrombocytopenia, autoimmune glomerulonephritis, and induced glomerulonephritis. Since the majority of human RF bind to the IgG Fc $C_H2$-$C_H3$ cleft (Sasso et al. (1988) *J. Immunol.* 140:3098-3107; Corper et al. supra; and Sohi et al. supra), polypeptides that bind to the $C_H2$-$C_H3$ cleft would directly inhibit the binding of RF to immune-complexed IgG Fc, and therefore would ameliorate the contribution of RF to The pathology of RA.

Systemic lupus erythematosus and lupus nephritis—SLE is a chronic autoimmune disease with many manifestations. The production of autoantibodies leads to immune complex formation and subsequent deposition in many tissues (e.g., glomeruli, skin, lungs, synovium, and mesothelium), leading to the manifestations of the disease. Renal disease is common with SLE because the immune complexes often are deposited in the renal glomeruli. Despite therapy, progression to chronic renal failure is common.

Lupus nephritis is an inflammation of the kidney that is caused by SLE-related glomerular deposition of immune complexes and FcγR (see, e.g., Clynes et al. (1998) *Science* 279:1052-1054). In mouse models of SLE, significant proteinuria also was observed concomitant with the serological appearance of antibodies to DNA and histones, as well as immune complexes of the IgG1, IgG2a, and IgG2b subclasses. The median survival is 6 months, and mortality results from renal failure. B cells and autoantibodies are thought to play essential roles in disease development, and agents that interfere with autoantibody production have been shown to attenuate the disease.

Studies of the role of the FcγRs have been facilitated by the availability of defined murine strains deficient in components of this pathway. The mouse strain $\gamma^{-/-}$, which is deficient in the FcR γ chain, does not express the activation receptors FcγRI and FcγRIII, but still bears the inhibitory receptor FcγRIIB. Mice lacking FcγRI or FcγRIII were protected from developing Lupus nephritis. Through a genetic disruption of the FcγR/immune complex interaction, Clynes et al. (supra) showed that the interaction of immune complex and cellular Fc receptors was essential to the development of Lupus nephritis. However, the mice lacking FcR still demonstrated significant renal immune complex deposition.

Histone H1 has been shown to bind to immune complexes (Gussin et al. (2000) *Ann. Rheum. Dis.* 59:351-358; and Costa et al. (1984) *J. Immunol. Methods* 74:283-291). Costa et al. also showed that rheumatoid factors competitively inhibited the binding of histone H1 to immune complexes, suggesting that the binding of histone H1 to immune complexes involves the IgG Fc $C_H2$-$C_H3$ cleft. Other studies showed that perfusion of rat kidneys with histones, DNA, and anti-DNA antibodies resulted in the deposition of DNA/anti-DNA immune complexes in the glomerular basement membrane (GBM), suggesting that immune complex binding to the GBM is directly mediated by the binding of histones to the GBM (Termaat et al. (1992) *Kidney Int.* 42:1363-1371; and Gussin et al. supra). The use of polypeptides that bind to the $C_H2$-$C_H3$ cleft would inhibit the binding of histones to immune-complexed IgG Fc, and therefore would ameliorate the contribution of these Fc-mediated immune complexes to the pathology of SLE and Lupus nephritis.

In a competitive inhibition study using IgG Fc fragments, both deposited IgG immune complexes and injected Fc fragments colocalized in the mesangium of Fc-treated nephritic animals, suggesting that the blockade of FcR could be the underlying mechanism of the beneficial effect of Fc fragments (Gómez-Guerrero et al. (2000) *J. Immunol.* 164:2092-2101). This study also demonstrated the central importance of immune complex to FcR interactions in mediating Lupus nephritis. In addition, the reduction of multiple inflammatory cytokines demonstrated the importance of preventing the inflammatory cascade rather than attempting to interfere with the cascade by inhibiting one or more inflammatory molecules. Polypeptides that bind to the $C_H2$-$C_H3$ cleft therefore also would inhibit the binding of FcR to immune-complexed IgG Fc, and would reduce the contribution of FcR to the pathology of SLE and Lupus nephritis.

Gómez-Guerrero et al. also demonstrated that, the elevated cholesterol observed in untreated nephritis mice (227±27 mg/dl) was reduced by more than half in nephritis mice treated with Fc fragments (103±16 mg/dl). Women between 35 and 44 years of age with systemic lupus erythematosus have a fifty times greater chance of developing advanced atherosclerosis/myocardial infarction than women of similar age without immune complex disease (Manzi et al. (2000) *Ann. Rheum. Dis.* 59:321-325). Although less dramatic, the same relationship holds true for patients with rheumatoid arthritis. The accelerated rate of atherosclerosis and myocardial infarction may be due to a chronic inflammatory state created by the formation of chronic immune complexes. The formation of these immune complexes can be prevented by inhibitory polypeptides that bind to the IgG Fc $C_H2$-$C_H3$ cleft.

Autoimmune glomerulonephritis—Autoimmune glomerulonephritis, a disorder related to lupus nephritis, is due to a T cell dependent polyclonal B cell activation that is responsible for production of antibodies against self components (e.g., GBM, imnmunoglobulins, DNA, myeloperoxydase) and non self components (e.g., sheep red blood cells and trinitrophenol). Increased serum IgE concentration is the hallmark of this disease.

Atherosclerosis—Atherosclerotic lesions are thought to be largely of an inflammatory nature. Recent studies have focused on the inflammatory component of atherosclerosis, attempting to highlight the differences between stable and unstable coronary plaques. An increasing body of evidence supports the hypothesis that atherosclerosis shares many similarities with other inflammatory/autoimmune diseases. Indeed, there are surprising similarities in the inflammatory/immunologic response observed in atherosclerosis, unstable angina, and rheumatoid arthritis, the prototype of autoimmune disease (Pasceri and Yeh (1999) *Circulation* 100(21): 2124-2126).

Activated macrophages and macrophage-derived foam cells laden with cholesterol esters are a major constituent of atherosclerotic lesions, and can influence lesion formation via several potential mechanisms. One such mechanism is FcγR activation and/or FcγR-mediated clearance of immune complexes containing cholesterol, such as lipoprotein immune complexes. Recent studies indicated that highly cellular preatheromatous lesions contain numerous macrophages in the zone of proliferation that express each class of FcγR (FcγRIA, FcγRIIA, and FcγRIIIA; (Ratcliffe et al. (2001) *Immunol. Lett.* 77:169-174). These data provided further support for the idea that FcγR-mediated clearance of immune complexes can occur in arterial lesions during atherogenesis. Expression of both the high affinity (FcγRIA) and lower affinity (FcγRIIA/FcγRIIIA) receptors indicated that mono- and multivalent IgG-containing immune complexes could engage FcγR and influence lesion formation through several different inflammatory mechanisms triggered by receptor activation.

There also appears to be an established link between chronic *Chlamydia pneumoniae* infections and atherosclerosis (Glader et al. (2000) *Eur. Heart J.* 21(8):639-646). The proatherogenic effects of *C. pneumoniae* lipoprotein may be enhanced and/or partly mediated through the formation of circulating immune complexes containing *C. pneumoniae*-specific IgG antibodies. The connection between chronic *C. pneumoniae* infections and atherosclerosis may be explained at least in part by an interaction with *C. pneumoniae* lipoprotein through the formation of circulating immune complexes. The $C_H2$-$C_H3$ binding polypeptides of the invention therefore also can be useful for treating elevated cholesterol levels and atherosclerosis/myocardial infarction.

Multiple sclerosis—MS is an autoimmune disease that attacks the insulating myelin sheath that surrounds neurons. This compromises conduction of nerve signals between the body and brain. Symptoms can be mild or severe, short or long in duration, and may include blurred vision, blindness, dizziness, numbness, muscle weakness, lack of coordination and balance, speech impediments, fatigue, tremors, sexual dysfunction, and bowel and bladder problems. Although many people have partial or complete remissions, symptoms for some progressively worsen with few or no remissions.

Research has suggested that patients with MS have ongoing systemic virus production with resultant immune complex formation. In addition, MS patients often have serum complexes containing brain-reactive components (Coyle and Procyk-Dougherty (1984) *Ann. Neurol.* 16:660-667). The etiology of MS may be multifactorial and involve abnormal immunological responses, possibly precipitated by infectious agents acquired during childhood by genetically susceptible individuals. The immunological responses include alterations in myelin basic protein concentration, antimyelin antibody and immune complex activities in CSF, and in vitro stimulation, suppression, and migration inhibition of blood lymphocytes. These responses appear to correlate with stage of MS and severity of CNS damage (Iivanainen (1981) *J. Neuroimmunol.* 1:141-172). Furthermore, levels of circulating immune complexes were found to be significantly increased in the sera of patients with progressive and active relapsing-remittent MS (Procaccia et al. (1988) *Acta Neurol. Scand.* 77:373-381). Immune complex levels also were found to be increased in the cerebrospinal fluid of MS patients at the relapsing-remittent stage.

Myelin basic protein (MBP) is important in the immunopathogenesis of MS. MBP has been shown to bind to immune complexes and immune-complexed IgG Fc (Sindic et al. supra). These immune complex binding sites were shown to be multivalent on MBP, and histones completely inhibited the agglutination of immune complexed IgG Fc latex-coated beads by MBP. In addition, certain FcR alleles have been correlated with the disease course of MS (Vedeler et al. (2001) *J. Neuroimmunol.* 118:187-193). The involvement of FcRs in. MS was further suggested by studies showing that FcRγ$^{-/-}$ mice were protected from experimental autoimmune encephalomyelitis, a model of MS induced by myelin oligodendrocyte glycoprotein (Abdul-Majid et al. (2002) *Scand. J Immunol.* 55:70-81). Treating an MS patient with polypeptides that bind to the $C_H2$-$C_H3$ cleft would inhibit the binding of MBP to immune-complexed IgG Fc and would interfere with immune complex binding to FcRs, therefore ameliorating the pathology of MS.

Parkinson's disease—The clinical symptoms of Parkinson's disease (PD) result from the death of dopaminergic neurons in a section of the brain known as the substantia nigra (SN). An overresponsive immune system may play a role in perpetuating PD by producing cytokines (e.g., interleukin-1 and tumor necrosis factor) in response to the initial damage, which can further injure cells in the brain. Furthermore, immunoglobulins from PD individuals have been shown to contribute to the pathogenesis of SN cells (Chen et al. (1998) *Arch. Neurol.* 55:1075-1080).

Tyrosine hydroxylase (TH) is the rate-limiting enzyme in the biosynthesis of catecholamine neurotransmitters and is expressed only in those neurons (e.g., the neurons of the SN) that normally synthesize and release such neurotransmitters. A structural analysis of TH suggests that immune complexes may bind to the enzyme and contribute to PD pathology. $C_H2$-$C_H3$ cleft-binding polypeptides therefore may be useful for treating PD by inhibiting Fc-mediated binding of immune complexes to TH.

Crohn's disease—Crohn's disease results in chronic inflammation of the gastrointestinal tract, usually the small intestine. It affects about 500,000 people in the United States, most often before age 30, causing mild to severe abdominal pain, diarrhea, fever and weight loss. While the cause of the disease is unknown, the prevailing theory is that in Crohn's patients, the intestinal immune system over-reacts to viral or bacterial agents and initiates ongoing, uncontrolled inflammation of the intestine. It has been suggested that immune complexes of the IgG class may activated inflammatory neutrophils in Crohn's disease (Nielsen et al. (1986) *Clin. Exp. Immunol.* 65:465-471).

RF and circulating immune complexes have been detected in the sera of Crohn's patients (Procaccia et al. (1990) *Boll Ist Sieroter Milan* 69:413-421; and Elmgreen et al. (1985) *Acta Med. Scand.* 218:73-78). The prevalence of IgG-containing immune complexes and increased IgG RF levels in these patients suggests that the inhibition of Fc-mediated immune complex formation would be useful for treating Crohn's disease.

Psoriasis—The release of cytokines such as interleukin-2 is thought to be involved in psoriasis. In this disease, cytokines signal skin cells to reproduce and mature at an accelerated rate, setting off other reactions such as the activation of additional T cells and the "recruiting" of T cells into the skin. The initial activation of T cells starts a cycle that eventually leads to the formation of psoriasis lesions on the surface of the skin.

The psoriasis-associated antigen, pso p27, is a major antigen in the immune reactions of psoriasis. The synthesis of this particular antigen is reduced with the remission of inflammation in psoriatic skin lesions. See Dalaker et al. (1999) *Acta Derm. Venereol.* 79:281-284. Rabbit antisera against pso p27 antigen from psoriatic scale reacted with the Fc region of human IgG. In addition, a commercial antiserum against human IgG recognized a component in the pso p27-containing solution used as the source of antigen for immunization of the rabbits (Asbakk et al. (1991) *APMIS* 99:551-556). The pso p27 antigen therefore may elicit the production of antibodies with rheumatoid factor activity in psoriatic patients.

Anti-IgG activity at the cellular level in psoriasis patients has been demonstrated using the so-called "rheumatoid" rosette test. The use of purified cell populations showed that the lymphocytes participating in the rheumatoid rosette phenomenon were lacking conventional T and B cell membrane markers. Such mononuclear cells bearing an FcR were able to act as killer cells to IgG-coated target cells. This cytotoxicity could contribute to the etiology of lesions in psoriasis (Clot et al. (1978) *Brit. J Derm.* 99:25-30). Inhibiting the binding of such lymphocytes to IgG molecules with a $C_H2$-$C_H3$ binding polypeptide therefore would be useful for treating psoriasis.

Ankylosing Spondylitis—Analysis of serum and synovial fluid samples from patients with ankylosing spondylitis (AS) and from healthy blood donors for the presence of antibodies cross-reacting with the Fc region of rabbit IgG revealed insignificant amounts of free RF, while IgG RF were observed in alkaline dissociated circulating immune complexes (CIC). Extensive amounts of IgG and moderate amounts of IgM reacting with pso p27 also were detected in alkaline dissociated CIC from the AS patients (Rodahl et al. (1988) *Ann. Rheum. Dis.* 47:628-633). Antigens related to pso p27 therefore appear to participate in CIC formation in AS, and may be responsible for the elicitation of RF in patients with AS.

Cancer—Scientific evidence indicates that factors which can bind to immunoglobulins can inhibit cancer metastasis (see, e.g., Mathiot et al. (1992) *Immunol. Res.* 11:296-304; and Hoover et al. (1990) *Curr. Top. Mircobiol. Immunol.* 166:77-85). Several key elements of the metastatic process can be inhibited by polypeptides and other compounds provided by the invention. Fc receptors on cancer cells have been implicated in cancer metastasis (see, e.g., Gergely et al. (1994) *Adv. Cancer Res.* 64:211; Wallace et al. (1994) *J. Leuk. Biol.* 55:816-823; and Witz and Ran. (1992) *Immunol. Res.* 11:283-295).

FcR positive tumor cells can bind to the Fc region of tumor-specific antibodies. FcRs thus can protect tumor cells by counteracting antibody-dependent effector functions such as complement-mediated-lysis or antibody-dependent cell-mediated cytotoxicity (Gergely et al. supra). In this manner, FcR expression endows tumor cells with the ability to escape immune mechanisms. The expression of FcRs on tumor cells also may facilitate growth of the cells. In addition, tumor cells may use FcRs to bind to adhesion molecules and cause localized inflammatory responses that lead to angiogenesis. Tumor cells transfected in vitro with FcγR showed higher rates of metastasis and tumorigenicity in vivo than cells that did not express the receptor (Witz and Ran supra). Use of a $C_H2$-$C_H3$ binding polypeptide to block interactions between immunoglobulin molecules and FcRs on cancer cells would be useful for preventing or reducing cancer metastasis.

Graft rejection following transplantation—$C_H2$-$C_H3$ binding polypeptides of the invention also are useful for preventing graft rejection following tissue or organ transplantation. Graft rejection typically results from the cumulative effects of both cell-mediated and humoral immune attacks on the grafted tissue. Solid organ (tissue) transplantation includes, for example, transfer of kidney, heart, lungs, liver, pancreas, skin, cornea, and bone. Bone marrow transplantation is employed in the treatment of conditions such as immunodeficiency disease, aplastic anemia, leukemia, lymphoma, and genetic disorders of hematopoiesis. Recent studies have suggested that FcR non-binding anti-CD3 monoclonal antibodies profoundly affect T cell function by delivering incomplete signals to activated T cells. These incomplete signals may result in functional inactivation of the inflammatory Th1 T cell subset that mediates graft rejection. $C_H2$-$C_H3$ binding polypeptides of the invention also maybe useful for blocking signals to activated T cells, thus inhibiting graft rejection.

The invention will be further described in the following examples, which does not limit the scope of the invention described in the claims.

EXAMPLES

Example 1

Figure 1B:
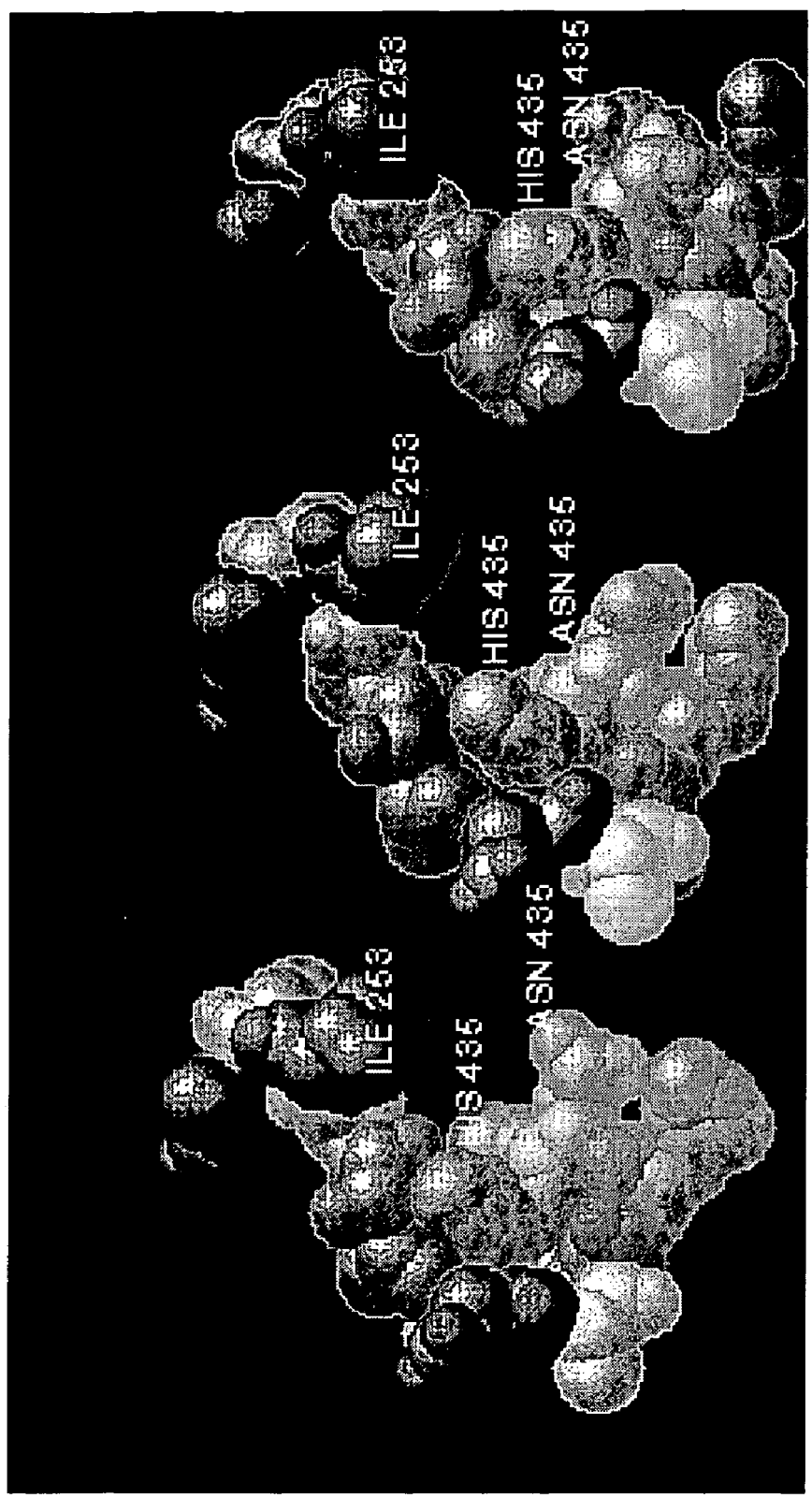

Modeling the Amino Acid Residues within the $C_H2$-$C_H3$ Cleft that are Important for Binding to a Test Polypeptide The first step in structure-based molecular drug design is determining the three-dimensional structure of the target receptor. Computer programs (e.g., RasMol 2.6, Protein Explorer, or Chime, each available from the University of Massachusetts Molecular Visualization web site on the internet) that display the three-dimensional structure of a test ligand, together with programs (e.g., Auto-dock or Dock) that display the exact three-dimensional structure of the target receptor, can be used to predict the structure of ligands that will bind to the target receptor. Three-dimensional structures can be produced by providing data consisting of the atomic coordinates of the target receptor and the test ligand to a computer that contains the appropriate software. FIGS. 1A and 1B show computer-generated, three-dimensional structures of an Fc $C_H2$-$C_H3$ cleft from an IgG molecule in both a non-complexed and an antigen-bound state, revealing the open and closed conformations described herein. The atomic coordinates of a $C_H2$-$C_H3$ cleft from IgG molecules complexed to a peptide ligand and a rheumatoid factor are shown in FIGS. 2A and 2B, respectively.

Figure 3:
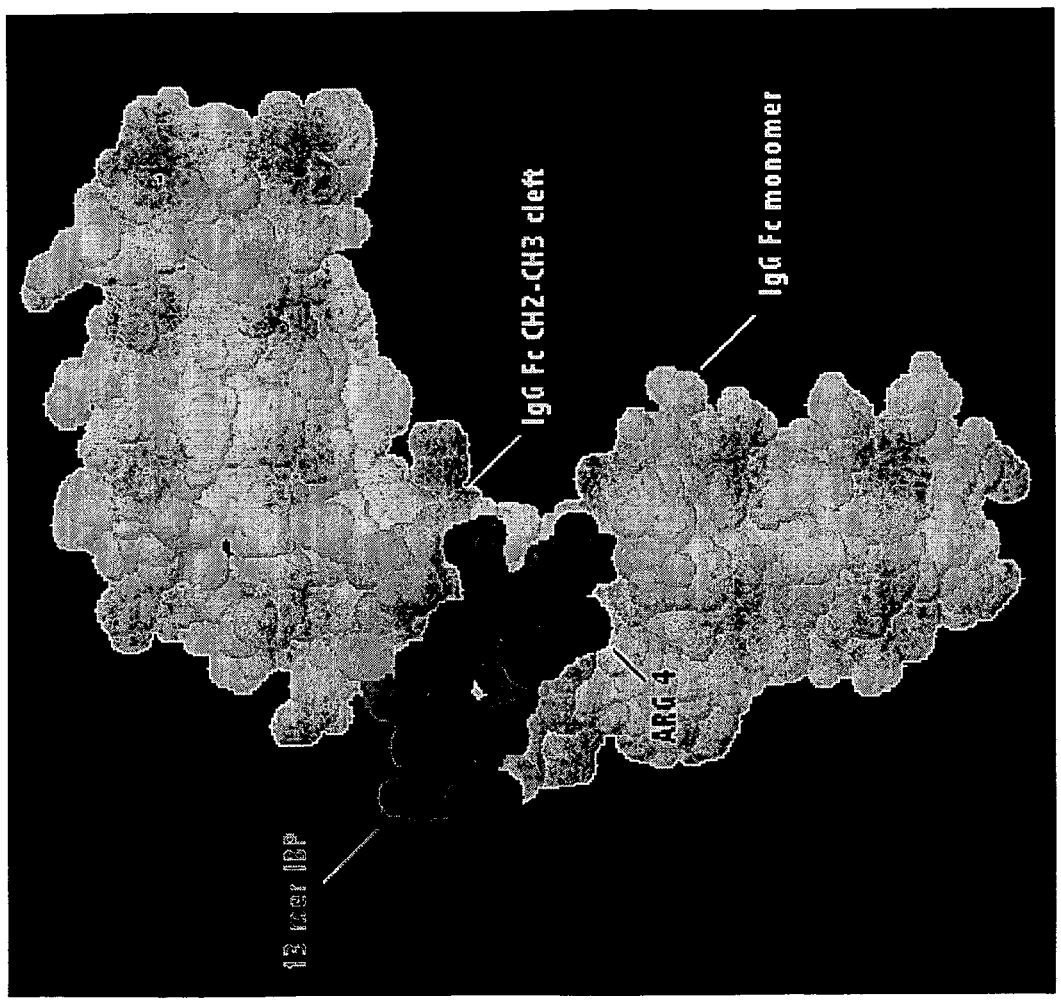

A computer-modeled examination of the interaction between an IgG Fc $C_H2$-$C_H3$ cleft and a polypeptide with the amino acid sequence Asp-Cys-Ala-Ala-His-Leu-Gly-Glu-Leu-Val-Trp-Cys-Thr (SEQ ID NO:4) showed that the Trp residue of the polypeptide could form a hydrogen bond to the cleft in between Ile253 of the $C_H2$ region and His435 of the $C_H3$ region (FIG. 3). The amino acids within the $C_H2$-$C_H3$ cleft that were critical for binding to this polypeptide were Leu251, Met252, Ile253, Ser254, His433; Asn434, His435, and Tyr436.

Example 2

Amino Acid Substitutions within the Polypeptide of Example 1

Examination of the polypeptide described above (SEQ ID NO:4) showed that substitution of Arg for Asp in the first position did not affect binding to the IgG Fc region. Replacement of the Trp in the fourth position with Arg also would not be expected to have a major impact on immunoglobulin binding. The substitution of one or both of these residues to Arg (e.g., as in SEQ ID NO:2) would be expected to make the polypeptide more water soluble, thereby increasing its bioavailability. A three-dimensional structure of this modified peptide bound to the Fc $C_H2$-$C_H3$ region is shown in FIG. 3.

Example 3

Molecular Modeling of a Small Ligand for the $C_H2$-$C_H3$ Cleft

Molecular modeling, based on the unique three-dimensional structure of the IgG Fc $C_H2$-$C_H3$ cleft, was used to predict small non-peptide ligands for the cleft. Using the atomic structural coordinates shown in FIGS. 2A and 2B, the polyphenol quercetin was shown to bind to the target conformation with a $K_d$ of 56 μM.

Example 4

In vitro Assays for Measuring Ligand binding to the $C_H2$-$C_H3$ Cleft

In vitro assays involving enzyme-linked immunosorbent assay (ELISA) and double immunodiffusion techniques are used to demonstrate competitive inhibition of immune complexed IgG Fc binding to factors such as FcR, RF, FcRn, C1q, histones, CII, and MBP by polypeptides and compounds of the invention. Standardized reagents and ELISA kits are useful to reduce costs and increase the reproducibility of the experiments.

In a standard ELISA, an antigen is immunoadsorbed onto a plastic microwell. After suitable blocking and washing, a primary antibody with specificity directed toward the antigen is added to the microwell. After another wash phase, a secondary antibody that is directed toward the primary antibody and conjugated to an enzyme marker such as horseradish peroxidase (HRP) is added to the microwell. Following another wash cycle, the appropriate enzyme substrate is added. If an antigen to primary antibody to secondary antibody/HRP conjugate is formed, the conjugated enzyme catalyzes a colorimetric chemical reaction with the substrate, which is read with a microplate reader or spectrophotometer. By standardizing the levels of the antigen and secondary antibody/HRP conjugate, a titer of the primary antibody (the variable) is established. In a standard ELISA system, the primary antibody binds to the antigen through its complementarity determining regions (CDR) located in the Fab arms. Likewise, the secondary antibody/HRP conjugate binds to the primary antibody via its CDR Fab region. Because the HRP is conjugated to the Fc region of the secondary antibody, direct Fc binding is very limited or abrogated.

For this reason, a "reverse ELISA" technique is used to assess binding of the Fc region to ligands that bind to immune complexed IgG Fc. In a reverse ELISA, the enzyme (e.g., HRP) is not covalently conjugated to the Fc portion of the secondary antibody. Rather, a preformed immune complex of peroxidase-rabbit (or mouse) anti-peroxidase IgG ("PAP" complex) is used. In this method, HRP serves as the enzyme marker but does not block the Fc region. In the reverse ELISA system, an Fc $C_H2$-$C_H3$ cleft binding ligand (e.g., purified human C1q) is bound to microwell plates. Soluble PAP complexes contain three HRP molecules for every two rabbit anti-peroxidase molecules (slight antigen excess). Such PAP complexes are available from, for example, Sigma Chemical Co. (St. Louis, Mo.) and Jackson Laboratories (Bar Harbor, Me.). In the absence of competitor, PAP complexes bind to the immobilized ligand and the reaction between HRP and its substrate produces a signal. This signal is reduced by polypeptides and compounds of the invention that inhibit PAP binding to the immobilized ligand.

Inhibition of C1q binding: Quidel Corporation (San Diego, Calif.) manufactures a circulating immune complex-C1q enzyme immunoassay (CIC-C1q EIA) that is used to detect CIC in human serum or plasma. The assay uses highly pure, functional human C1q coated in the solid phase to capture immune complexes. In the first stage, CIC in the diluted patient samples and heat aggregated IgG (HAGG) in the controls and standards are dispensed into C1q coated assay wells. After incubation, unbound material is removed in a washing step and a ready to use conjugate (goat anti-human Ig-HRP) is added. After a second incubation, unbound conjugate is washed away. Substrate is added for a short incubation interval, and the quantity of CIC in the sample (μg Eq/mL) is determined by comparison to a standard curve.

The effectiveness of polypeptides and compounds of the invention as competitive inhibitors of the positive control (HAGG) is tested in this system. Alternatively, preformed immune complexes (PAP) are used to validate the reverse ELISA system. Human C1q binds to rabbit PAP immune complexes (Koroleva et al. (1998) *FEMS Immunol. Med. Microbiol.* 20:11-20), and the substitution of rabbit PAP immune complexes for human immune complexes is straightforward. Once the reverse ELISA system is optimized, simple competitive inhibition experiments using polypeptides of the invention are conducted to demonstrate that they inhibit C I q binding to immune complexes.

Inhibition of FcR binding: Once the reverse ELISA protocol is established using the C1q assay, the assay is redesigned using FcγIIa, FcγIIb and FcγIII in place of C1q. Highly purified FcγIIa, FcγIIb and FcγIII are immunoadsorbed onto plastic microwells. After optimizing the FcγR reverse ELISA system, simple competitive inhibition experiments using polypeptides of the invention are conducted to demonstrate that they inhibit the binding of immune complexes to purified FcγR.

The cellular assay of Sulica et al. ((1979) *Immunol.* 38:173-179), involving the binding of rabbit PAP immune complexes for U937 monocytes, is also used to examine the ability of polypeptides of the invention to inhibit interactions between immune complexes and FcRs. U937 monocytes expressing FcγRI and FcγRIII are suspended with preformed PAP in the presence and absence of polypeptides and compounds of the invention. After a suitable incubation period, the cells are repeatedly centrifuged and washed. Immune complexed PAP bound to U937 cells are suspended with the HRP substrate, and after incubation the cells are centrifuged, the supernatant is transferred to microwells, and the absorbance is read by a microplate reader.

Inhibition of RF binding: The assay to test RF binding to IgG Fc $C_H2$-$C_H3$ clefts is very similar to the C1q-CIC EIA assay described above, with the exception that polyclonal IgM RF is coated onto the microwells instead of C1q. After optimization, the same competitive inhibition techniques as described for the C1q-CIC EIA are used to demonstrate inhibition of polyclonal RF to immune complex binding. High titer, RF positive sera are purchased from Research Diagnostics (Flanders, N.J.).

Inhibition of Fc:Fc interactions: The Fc region of IgG4 interacts in an Fc to Fc fashion with immune complexed IgG. Purified IgG4 and hRF-1 (an IgG4 RF) are used with polypeptides of the invention to examine inhibition of immune complex formation and Fc:Fc interactions. Chemical modification of His435, a critical IgG Fc amino acid bound by polypeptides of the invention, is known to inhibit Fc:Fc interactions.

The assay to test the ability of polypeptides of the invention to interfere with Fc:Fc binding is very similar to the C1q-CIC EIA assay described above, with the exception that whole human IgG4 is coated onto the microwells instead of C1q. After optimizing this CIC assay, the same competitive inhibition techniques as described for the C1q-CIC EIA are used to demonstrate inhibition of IgG4 Fc:Fc or IgG4 hRF-1 immune complex binding.

Inhibition of histone binding: The binding of immune complexes to the kidneys in lupus nephritis appears to involve (a) the binding of histones to the GBM, and then (b) the binding of immune complexes (through the IgG Fc $C_H2$-$C_H3$ cleft) to the bound histones. Experiments similar to those described above are used to inhibit of histone to IgG Fc binding. Highly purified histones are available from Sigma Chemical Co. The assay to test the ability of polypeptides of the invention to interfere with histone binding to immune complexes is very similar to the C1q-CIC EIA assay described above, with the exception that histones were coated onto the microwells instead of C1q. After optimizing this CIC assay, the same competitive inhibition techniques as described for the C1q-CIC EIA are used to demonstrate inhibition of histone binding to immune complexes.

Inhibition of Collagen II, MBP, and FcRn binding: Polypeptides of the invention also are tested for their ability to inhibit (a) binding of CII to anti-CII antibodies, (b) binding of MBP to immune complexes, and (c) binding of FcRn to immune complexes. The assay to test the ability of polypeptides of the invention to interfere with such binding is very similar to the C1q-CIC EIA assay described above, with the exception that the microwells are coated with CII, MBP, or FcRn instead of C1q. The immunodominate CII peptide is a small linear peptide and is readily synthesized, and purified CII extracts also are commercially available. Purified MBP is available commercially. After optimization, the same competitive inhibition techniques as described for the C1q-CIC EIA are used to demonstrate inhibition of binding.

Example 5

In vivo Assays for Assessing Inhibition of Fc-mediated Immune Complex Formation in a Mouse Model of RA The inhibitory effects of polypeptides of the invention also are tested in animal models of CII-induced arthritis. Arthritis prone DBA/1 mice are injected intradermally with 100 μg of bovine CII emulsified in Complete Fruends Adjuvant. These mice typically develop RA-like disease after 60 days. Mice are divided into three groups: (1) a control group that is expected to develop arthritis; (2) a group treated with polypeptides or compounds of the invention at the time of CII immunization; and (3) a group treated with polypeptides or compounds of the invention beginning 45-60 days after CII immunization, in mice that have already started showing signs of arthritis. Symptoms of arthritis before and after treatment are monitored to determine the in vivo effectiveness of polypeptides and compounds of the invention.

Example 6

In vivo Assays for Assessing Inhibition of Fc-mediated Immune Complex Formation in a Mouse Model of SLE MRL/MpJ-Fas (MRL/1pr) mice develop a syndrome that is serologically and pathologically similar to human SLE. These mice have high levels of IgG autoantibodies to nuclear antigens such as single-stranded and double-stranded DNA, and also exhibit progressive glomerulonephritis as a result of in vivo immune complex formation and deposition in the glomerulus of the kidneys. At seven weeks of age, MRL/1pr mice are treated with biweekly intraperitoneal injections of the polypeptides described herein. Levels of proteinuria are measured once weekly for forty weeks. Animals treated with the polypeptides typically have significantly lower levels of proteinuria. After forty weeks, renal biopsies are conducted to demonstrate that the treated animals have significantly less glomerulonephritis and IgG immune complex deposition. In addition, the mean survival of the treated animals is significantly increased. Similar results are obtained with (NZB× NZW)F1 mice, another murine model of SLE.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of designing a ligand having specific binding affinity for the $C_H2$-$C_H3$ cleft of an immunoglobulin molecule having bound antigen, said method comprising:

a) providing data to a specifically programmed computer, said data comprising the atomic coordinates of the amino acid residues at positions 252, 253, 435, and 436 within said $C_H2$-$C_H3$ cleft, and said computer having a computer program capable of generating an atomic model of a molecule from said atomic coordinate data;

b) generating with said computer an atomic model of said $C_H2$-$C_H3$ cleft;

c) providing to said computer data comprising the atomic coordinates of a candidate compound;

d) generating with said computer an atomic model of said candidate compound optimally positioned in said $C_H2$-$C_H3$ cleft;

e) outputting to a display said atomic model of said candidate compound optimally positioned in said $C_H2$-$C_H3$ cleft;

f) determining whether said optimally positioned candidate compound interacts with said amino acid residues within said $C_H2$-$C_H3$ cleft; and g) identifying said candidate compound as a ligand having specific binding affinity for said $C_H2$-$C_H3$ cleft if said candidate compound interacts with said amino acid residues.

2. The method of claim 1, wherein said atomic coordinates are provided in FIG. 2A or FIG. 2B.

3. The method of claim 1, wherein said ligand has a binding affinity of at least 1 μM for said $C_H2$-$C_H3$ cleft.

4. The method of claim 3, wherein said binding affinity is at least 100 nM.

5. The method of claim 3, wherein said binding affinity is at least 10 nM.

6. The method of claim 1, wherein said ligand does not detectably bind to another biological molecule when bound to said $C_H2$-$C_H3$ cleft.

7. The method of claim 6, wherein said another biological molecule comprises a $C_H2$-$C_H3$ cleft.

8. The method of claim 1, wherein said ligand is capable of inhibiting the Fc-mediated formation of an immune complex.

9. The method of claim 1, wherein said ligand is capable of inhibiting the binding of rheumatoid factors to said $C_H2$-$C_H3$ cleft.

10. The method of claim 1, wherein said ligand is capable of inhibiting the binding of histones to said $C_H2$-$C_H3$ cleft.

11. The method of claim 1, wherein said ligand is capable of inhibiting the binding of FcR to said $C_H2$-$C_H3$ cleft.

12. The method of claim 1, wherein said ligand is capable of inhibiting the binding of C1q to said $C_H2$-$C_H3$ cleft.

13. The method of claim 1, wherein said ligand is capable of inhibiting the binding of myelin basic protein to said $C_H2$-$C_H3$ cleft.

14. The method of claim 1, wherein said ligand is capable of inhibiting the binding of pso p27 to said $C_H2$-$C_H3$ cleft, a rheumatoid factor, or other autoantibodies.

15. The method of claim 1, wherein said ligand is a polypeptide.

16. The method of claim 15, wherein said polypeptide is 11 to 50 amino acids in length.

17. The method of claim 1, wherein said data of step (a) further comprise the atomic coordinates of one or more other amino acid residues.

18. The method of claim 17, wherein said atomic coordinates of said other amino acid residues are provided in FIG. 2A or FIG. 2B.

19. A method of designing a ligand having specific binding affinity for the $C_H2$-$C_H3$ cleft of an immunoglobulin molecule having bound antigen, said method comprising:

a) providing to a specifically programmed computer data comprising the atomic coordinates of a candidate compound, said computer having stored in memory thereon an atomic model of said $C_H2$-$C_H3$ cleft, wherein said model incorporates the atomic coordinates of the amino acid residues at positions 252, 253, 435, and 436 of said immunoglobulin molecule;

b) generating with said computer an atomic model of said candidate compound optimally positioned in said $C_H2$-$C_H3$ cleft;

c) outputting to a display said atomic model of said candidate compound optimally positioned in said $C_H2$-$C_H3$ cleft;

d) determining whether said optimally positioned candidate compound interacts with said amino acid residues within said $C_H2$-$C_H3$ cleft; and d) identifying said candidate compound as a ligand having specific binding affinity for said $C_H2$-$C_H3$ cleft if said candidate compound interacts with said amino acid residues.

20. The method of claim 19, wherein said atomic coordinates of said immunoglobulin molecule are provided in FIG. 2A or FIG. 2B.

21. The method of claim 1, wherein said computer comprises an atomic structural modeling program.

22. The method of claim 21, wherein said structural modeling program is selected from the group consisting of Ras-Mol, INSIGHT, GRASP, Dock, Auto-Dock, Protein Explorer, and Chime.

23. The method of claim 19, wherein said computer comprises an atomic structural modeling program.

24. The method of claim 23, wherein said structural modeling program is selected from the group consisting of Ras-Mol, INSIGHT, GRASP, Dock, Auto-Dock, Protein Explorer, and Chime.

* * * * *

UNITED STATES PATENT AND TRADEMARK OFFICE
CERTIFICATE OF CORRECTION

PATENT NO.        : 7,584,059 B2
APPLICATION NO.   : 11/061065
DATED             : September 1, 2009
INVENTOR(S)       : Neil M. Bodie It is certified that error appears in the above-identified patent and that said Letters Patent is hereby corrected as shown below:

Title Page, item 73 Assignee, please delete "Therapeuties" and insert --Therapeutics-- therefor.

Signed and Sealed this

Third Day of November, 2009

David J. Kappos
*Director of the United States Patent and Trademark Office*

SEQUENCE LISTING

<160> NUMBER OF SEQ ID NOS: 4

<210> SEQ ID NO 1
<211> LENGTH: 13
<212> TYPE: PRT
<213> ORGANISM: Artificial Sequence
<220> FEATURE:
<223> OTHER INFORMATION: Synthetically generated polypeptide
<220> FEATURE:
<221> NAME/KEY: VARIANT
<222> LOCATION: 1
<223> OTHER INFORMATION: Xaa = Absent or any amino acid
<220> FEATURE:
<221> NAME/KEY: VARIANT
<222> LOCATION: 4
<223> OTHER INFORMATION: Xaa = Any amino acid, except any non-aromatic
      amino acid such as Trp, Phe, Tyr, or Ala
<220> FEATURE:
<221> NAME/KEY: VARIANT
<222> LOCATION: 6
<223> OTHER INFORMATION: Xaa = Any amino acid
<220> FEATURE:
<221> NAME/KEY: VARIANT
<222> LOCATION: 7
<223> OTHER INFORMATION: Xaa = Gly or Ala
<220> FEATURE:
<221> NAME/KEY: VARIANT
<222> LOCATION: 8
<223> OTHER INFORMATION: Xaa = Glu or Ala
<220> FEATURE:
<221> NAME/KEY: VARIANT
<222> LOCATION: 13
<223> OTHER INFORMATION: Xaa = Absent or any non-aromatic amino acid

<400> SEQUENCE: 1

Xaa Cys Ala Xaa His Xaa Xaa Xaa Leu Val Trp Cys Xaa
 1               5                  10

<210> SEQ ID NO 2
<211> LENGTH: 13
<212> TYPE: PRT
<213> ORGANISM: Artificial Sequence
<220> FEATURE:
<223> OTHER INFORMATION: Synthetically generated polypeptide

<400> SEQUENCE: 2

Arg Cys Ala Arg His Leu Gly Glu Leu Val Trp Cys Thr
 1               5                  10

<210> SEQ ID NO 3
<211> LENGTH: 11
<212> TYPE: PRT
<213> ORGANISM: Artificial Sequence
<220> FEATURE:
<223> OTHER INFORMATION: Synthetically generated polypeptide
<220> FEATURE:
<221> NAME/KEY: VARIANT
<222> LOCATION: 3
<223> OTHER INFORMATION: Xaa = Any amino acid, except any non-aromatic
      amino acid such as Trp, Phe, Tyr, or Ala
<220> FEATURE:
<221> NAME/KEY: VARIANT
<222> LOCATION: 5
<223> OTHER INFORMATION: Xaa = Any amino acid
<220> FEATURE:
<221> NAME/KEY: VARIANT
<222> LOCATION: 6
<223> OTHER INFORMATION: Xaa = Gly or Ala
<220> FEATURE:
<221> NAME/KEY: VARIANT
<222> LOCATION: 7
<223> OTHER INFORMATION: Xaa = Glu or Ala -continued

```
<400> SEQUENCE: 3

Cys Ala Xaa His Xaa Xaa Xaa Leu Val Trp Cys
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetically generated polypeptide

<400> SEQUENCE: 4

Asp Cys Ala Ala His Leu Gly Glu Leu Val Trp Cys Thr
1               5                   10
```